US010208357B2

(12) United States Patent
Yu

(10) Patent No.: US 10,208,357 B2
(45) Date of Patent: Feb. 19, 2019

(54) CELL BASED ASSAY

(71) Applicant: Medical Diagnostic Laboratories, L.L.C., Hamilton, NJ (US)

(72) Inventor: Yick Loi Raymond Yu, East Brunswick, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

(21) Appl. No.: 15/464,520

(22) Filed: Mar. 21, 2017

(65) Prior Publication Data

US 2018/0274043 A1 Sep. 27, 2018

(51) Int. Cl.

*C12Q 1/6897* (2018.01)
*G01N 33/50* (2006.01)

(52) U.S. Cl.

CPC ....... *C12Q 1/6897* (2013.01); *G01N 33/5011* (2013.01); *G01N 2333/912* (2013.01)

(58) Field of Classification Search

None
See application file for complete search history.

(56) References Cited

U.S. PATENT DOCUMENTS 7,981,418 B2 * 7/2011 Amler .............. A61K 39/39558 424/138.1

OTHER PUBLICATIONS

Yuan et al., Heregulin-β promotes matrix metalloproteinase-7 expression via HER2-mediated AP-1 activation in MCF-7 cells 318 Molecular and Cellular Biochemistry 73-79 (2008).*
Bose, Ron, et al., Activating HER2 Mutations in HER2 Gene Amplification Negative Breast Cancer, Cancer Discov.; Feb. 2013; 3(2): 224-237.
Zachary, C.Hartman, et Al., HER2 Overexpression Elicits a Proinflammatory IL-6 Autocrine Signaling Loop that is Critical for Tumorigenesis; Cancer Res. Jul. 1, 2011; 71(13): 4380-4391.

* cited by examiner

*Primary Examiner* — Nancy J Leith
(74) *Attorney, Agent, or Firm* — Terence J. Bogie

(57) ABSTRACT

The present invention relates to cell-based assays involving HER2. The assays use assay cells that are transfected with cassettes containing the HER2 gene of interest and measure the effect of mutations on the activity of HER2, and on their response to inhibitors.

16 Claims, 31 Drawing Sheets

Specification includes a Sequence Listing.

A)

B)

A)

All-in-one

Addition of DNA/Transfection mix and NRG1

24 hours

B)

A)

B)

| Inhibitors | % of activity |
| --- | --- |
| Lapatinib 20 nM | 77% |
| Lapatinib 80 nM | 21% |
| Trastuzumab 0.1 ug/ml | 67% |
| Trastuzumab 0.5 ug/ml | 23% |
| Pertuzumab 0.1 ug/ml | 73% |
| Pertuzumab 0.5 ug/ml | 21% |

A)

B)

| Inhibitors | % of activity |
|---|---|
| Lapatinib 20 nM | 118% |
| Lapatinib 80 nM | 117% |
| Trastuzumab 0.1 ug/ml | 90% |
| Trastuzumab 0.5 ug/ml | 68% |
| Pertuzumab 0.1 ug/ml | 90% |
| Pertuzumab 0.5 ug/ml | 66% |

A)

B)

| Inhibitors | % of activity |
|---|---|
| Lapatinib 20 nM | 90% |
| Lapatinib 80 nM | 78% |
| Trastuzumab 0.1 ug/ml | 90% |
| Trastuzumab 0.5 ug/ml | 87% |
| Pertuzumab 0.1 ug/ml | 101% |
| Pertuzumab 0.5 ug/ml | 105% |

A)

B)

| Inhibitors | % of activity |
| --- | --- |
| Lapatinib 20 nM | 95% |
| Lapatinib 80 nM | 93% |
| Trastuzumab 0.1 ug/ml | 68% |
| Trastuzumab 0.5 ug/ml | 33% |
| Pertuzumab 0.1 ug/ml | 86% |
| Pertuzumab 0.5 ug/ml | 37% |

SEQUENCE LISTING

<160> NUMBER OF SEQ ID NOS: 31

<210> SEQ ID NO 1
<211> LENGTH: 36
<212> TYPE: DNA
<213> ORGANISM: Homo sapiens

<400> SEQUENCE: 1
tggctagccg ccaccatgcg accctccggg acggcc 36

<210> SEQ ID NO 2
<211> LENGTH: 29
<212> TYPE: DNA
<213> ORGANISM: Homo sapiens

<400> SEQUENCE: 2
gactcgagtc atgctccaat aaattcact 29

<210> SEQ ID NO 3
<211> LENGTH: 36
<212> TYPE: DNA
<213> ORGANISM: Homo sapiens

<400> SEQUENCE: 3
tggctagccg ccaccatgga gctggcggcc ttgtgc 36

<210> SEQ ID NO 4
<211> LENGTH: 29
<212> TYPE: DNA
<213> ORGANISM: Homo sapiens

<400> SEQUENCE: 4
gactcgagtc acactggcac gtccagacc 29

<210> SEQ ID NO 5
<211> LENGTH: 36
<212> TYPE: DNA
<213> ORGANISM: Homo sapiens

<400> SEQUENCE: 5
tggctagccg ccaccatgag ggcgaacgac gctctg 36

<210> SEQ ID NO 6
<211> LENGTH: 29
<212> TYPE: DNA
<213> ORGANISM: Homo sapiens

<400> SEQUENCE: 6
cctctagatt acgttctctg ggcattagc 29

<210> SEQ ID NO 7
<211> LENGTH: 39
<212> TYPE: DNA
<213> ORGANISM: Homo sapiens

<400> SEQUENCE: 7
gcgttcgcta agcgtagcta gcgatgtacg ggccagata 39

<210> SEQ ID NO 8
<211> LENGTH: 21
<212> TYPE: DNA
<213> ORGANISM: Homo sapiens

<400> SEQUENCE: 8
gcgttcgcta agcgtagcta g 21

<210> SEQ ID NO 9
<211> LENGTH: 42
<212> TYPE: DNA
<213> ORGANISM: Homo sapiens

<400> SEQUENCE: 9
tctgatacgt ctcgacgcac tctcccagca tgcctgctat tg 42

<210> SEQ ID NO 10
<211> LENGTH: 22
<212> TYPE: DNA
<213> ORGANISM: Homo sapiens

<400> SEQUENCE: 10
tctgatacgt ctcgacgcac tc 22

<210> SEQ ID NO 11
<211> LENGTH: 39
<212> TYPE: DNA
<213> ORGANISM: Homo sapiens

<400> SEQUENCE: 11
ccagtggcca tcaaagtgtc cagggaaaac acatccccc 39

<210> SEQ ID NO 12
<211> LENGTH: 39
<212> TYPE: DNA
<213> ORGANISM: Homo sapiens

<400> SEQUENCE: 12
gggggatgtg ttttccctgg acactttgat ggccactgg 39

<210> SEQ ID NO 13
<211> LENGTH: 45
<212> TYPE: DNA
<213> ORGANISM: Homo sapiens

<400> SEQUENCE: 13
gctggtgtgg gctccccagg ttctccctat gtctcccgcc ttctg 45

<210> SEQ ID NO 14
<211> LENGTH: 45
<212> TYPE: DNA
<213> ORGANISM: Homo sapiens

<400> SEQUENCE: 14
cagaaggcgg gagacatagg gagaacctgg ggagcccaca ccagc 45

<210> SEQ ID NO 15
<211> LENGTH: 39
<212> TYPE: DNA
<213> ORGANISM: Homo sapiens

<400> SEQUENCE: 15
cccaaccatg tcaaaattgc agacttcggg ctggctcgg 39

<210> SEQ ID NO 16
<211> LENGTH: 39
<212> TYPE: DNA
<213> ORGANISM: Homo sapiens

<400> SEQUENCE: 16
ccgagccagc ccgaagtctg caattttgac atggttggg 39

<210> SEQ ID NO 17
<211> LENGTH: 57
<212> TYPE: DNA
<213> ORGANISM: Homo sapiens

<400> SEQUENCE: 17
tcgagggatg tccatattag gaggatgtcc atattaggag gatgtccata ttaggaa 57

<210> SEQ ID NO 18
<211> LENGTH: 57
<212> TYPE: DNA
<213> ORGANISM: Homo sapiens

<400> SEQUENCE: 18
agctttccta atatggacat cctcctaata tggacatcct cctaatatgg acatccc 57

<210> SEQ ID NO 19
<211> LENGTH: 84
<212> TYPE: DNA
<213> ORGANISM: Homo sapiens

<400> SEQUENCE: 19
tcgaggatca agtaaacaac tatgtaaaca agatcaagta aacaactatg taaacaagat 60
caagtaaaca actatgtaaa caaa 84

<210> SEQ ID NO 20
<211> LENGTH: 84
<212> TYPE: DNA
<213> ORGANISM: Homo sapiens

<400> SEQUENCE: 20
agcttttgtt tacatagttg tttacttgat cttgtttaca tagttgttta cttgatcttg 60
tttacatagt tgtttacttg atcc 84

<210> SEQ ID NO 21
<211> LENGTH: 30
<212> TYPE: DNA
<213> ORGANISM: Homo sapiens

<400> SEQUENCE: 21
tcgagtgagt cagtgagtca gtgagtcaga 30

<210> SEQ ID NO 22
<211> LENGTH: 30
<212> TYPE: DNA
<213> ORGANISM: Homo sapiens

<400> SEQUENCE: 22
agcttctgac tcactgactc actgactcac 30

<210> SEQ ID NO 23
<211> LENGTH: 36
<212> TYPE: DNA
<213> ORGANISM: Homo sapiens

<400> SEQUENCE: 23
tcgaggggac tttccgggac tttccgggac tttcca 36

<210> SEQ ID NO 24
<211> LENGTH: 36
<212> TYPE: DNA
<213> ORGANISM: Homo sapiens

<400> SEQUENCE: 24
agcttggaaa gtcccggaaa gtcccggaaa gtcccc 36

<210> SEQ ID NO 25
<211> LENGTH: 26
<212> TYPE: DNA
<213> ORGANISM: Homo sapiens

<400> SEQUENCE: 25
ctgagtcagt gagtcagtga gtcagc 26

<210> SEQ ID NO 26
<211> LENGTH: 34
<212> TYPE: DNA
<213> ORGANISM: Homo sapiens

<400> SEQUENCE: 26
tcgagctgac tcactgactc actgactcag gtac 34

<210> SEQ ID NO 27
<211> LENGTH: 20
<212> TYPE: DNA
<213> ORGANISM: Homo sapiens

<400> SEQUENCE: 27
tttcttccag tttgccaagg 20

<210> SEQ ID NO 28
<211> LENGTH: 20
<212> TYPE: DNA
<213> ORGANISM: Homo sapiens

<400> SEQUENCE: 28
acgattcctg ctcagcttgt 20

<210> SEQ ID NO 29
<211> LENGTH: 20
<212> TYPE: DNA
<213> ORGANISM: Homo sapiens

<400> SEQUENCE: 29
gcaaagggtt tgagtgaagg 20

<210> SEQ ID NO 30
<211> LENGTH: 20
<212> TYPE: DNA
<213> ORGANISM: Homo sapiens

<400> SEQUENCE: 30
gccactatgg gagaaaggtg 20

<210> SEQ ID NO 31
<211> LENGTH: 3283
<212> TYPE: DNA
<213> ORGANISM: Homo sapiens

<400> SEQUENCE: 31
ggcctaactg gccggtacct gagtcagtga gtcagtgagt cagctcgagt gagtcagtga 60

-continued

```
gtcagtgagt cagaagctta gacactagag ggtatataat ggaagctcga cttccagctt    120
ggcaatccgg tactgttggt aaagccacca tggtcttcac actcgaagat ttcgttgggg    180
actggcgaca gacagccggc tacaacctgg accaagtcct tgaacaggga ggtgtgtcca    240
gtttgtttca gaatctcggg gtgtccgtaa ctccgatcca aaggattgtc ctgagcggtg    300
aaaatgggct gaagatcgac atccatgtca tcatcccgta tgaaggtctg agcggcgacc    360
aaatgggcca gatcgaaaaa atttttaagg tggtgtaccc tgtggatgat catcacttta    420
aggtgatcct gcactatggc acactggtaa tcgacggggt tacgccgaac atgatcgact    480
atttcggacg gccgtatgaa ggcatcgccg tgttcgacgg caaaaagatc actgtaacag    540
ggaccctgtg gaacggcaac aaaattatcg acgagcgcct gatcaacccc gacggctccc    600
tgctgttccg agtaaccatc aacggagtga ccggctggcg gctgtgcgaa cgcattctgg    660
cgaattctca cggctttccg cctgaggttg aagagcaagc cgccggtaca ttgcctatgt    720
cctgcgcaca agaaagcggt atggaccggc acccagccgc ttgtgcttca gctcgcatca    780
acgtctaagg ccgcgactct agagtcgggg cggccggccg cttcgagcag acatgataag    840
atacattgat gagtttggac aaaccacaac tagaatgcag tgaaaaaaat gctttatttg    900
tgaaatttgt gatgctattg ctttatttgt aaccattata agctgcaata aacaagttaa    960
caacaacaat tgcattcatt ttatgtttca ggttcagggg gaggtgtggg aggtttttta   1020
aagcaagtaa aacctctaca aatgtggtaa aatcgataag gatccgtcga ccgatgccct   1080
tgagagcctt caacccagtc agctccttcc ggtgggcgcg gggcatgact atcgtcgccg   1140
cacttatgac tgtcttcttt atcatgcaac tcgtaggaca ggtgccggca gcgctcttcc   1200
gcttcctcgc tcactgactc gctgcgctcg gtcgttcggc tgcggcgagc ggtatcagct   1260
cactcaaagg cggtaatacg gttatccaca gaatcagggg ataacgcagg aaagaacatg   1320
tgagcaaaag gccagcaaaa ggccaggaac cgtaaaaagg ccgcgttgct ggcgtttttc   1380
cataggctcc gcccccctga cgagcatcac aaaaatcgac gctcaagtca gaggtggcga   1440
aacccgacag gactataaag ataccaggcg tttccccctg gaagctccct cgtgcgctct   1500
cctgttccga ccctgccgct taccggatac ctgtccgcct ttctcccttc gggaagcgtg   1560
gcgctttctc atagctcacg ctgtaggtat ctcagttcgg tgtaggtcgt tcgctccaag   1620
ctgggctgtg tgcacgaacc ccccgttcag cccgaccgct gcgccttatc cggtaactat   1680
cgtcttgagt ccaacccggt aagacacgac ttatcgccac tggcagcagc cactggtaac   1740
aggattagca gagcgaggta tgtaggcggt gctacagagt tcttgaagtg gtggcctaac   1800
tacggctaca ctagaagaac agtatttggt atctgcgctc tgctgaagcc agttaccttc   1860
ggaaaaagag ttggtagctc ttgatccggc aaacaaacca ccgctggtag cggtggtttt   1920
tttgtttgca agcagcagat tacgcgcaga aaaaaaggat ctcaagaaga tcctttgatc   1980
ttttctacgg ggtctgacgc tcagtggaac gaaaactcac gttaagggat tttggtcatg   2040
agattatcaa aaaggatctt cacctagatc cttttaaatt aaaaatgaag ttttaaatca   2100
atctaaagta tatatgagta aacttggtct gacagcggcc gcaaatgcta aaccactgca   2160
gtggttacca gtgcttgatc agtgaggcac cgatctcagc gatctgccta tttcgttcgt   2220
ccatagtggc ctgactcccc gtcgtgtaga tcactacgat tcgtgagggc ttaccatcag   2280
gccccagcgc agcaatgatg ccgcgagagc cgcgttcacc ggcccccgat ttgtcagcaa   2340
tgaaccagcc agcagggagg gccgagcgaa gaagtggtcc tgctactttg tccgcctcca   2400
tccagtctat gagctgctgt cgtgatgcta gagtaagaag ttcgccagtg agtagtttcc   2460
```

-continued

```
gaagagttgt ggccattgct actggcatcg tggtatcacg ctcgtcgttc ggtatggctt   2520

cgttcaactc tggttcccag cggtcaagcc gggtcacatg atcacccata ttatgaagaa   2580

atgcagtcag ctccttaggg cctccgatcg ttgtcagaag taagttggcc gcggtgttgt   2640

cgctcatggt aatggcagca ctacacaatt ctcttaccgt catgccatcc gtaagatgct   2700

tttccgtgac cggcgagtac tcaaccaagt cgttttgtga gtagtgtata cggcgaccaa   2760

gctgctcttg cccggcgtct atacgggaca acaccgcgcc acatagcagt actttgaaag   2820

tgctcatcat cgggaatcgt tcttcggggc ggaaagactc aaggatcttg ccgctattga   2880

gatccagttc gatatagccc actcttgcac ccagttgatc ttcagcatct tttactttca   2940

ccagcgtttc ggggtgtgca aaaacaggca agcaaaatgc cgcaaagaag ggaatgagtg   3000

cgacacgaaa atgttggatg ctcatactcg tcctttttca atattattga agcatttatc   3060

agggttacta gtacgtctct caaggataag taagtaatat taaggtacgg gaggtattgg   3120

acaggccgca ataaaatatc tttattttca ttacatctgt gtgttggttt tttgtgtgaa   3180

tcgatagtac taacatacgc tctccatcaa aacaaaacga aacaaaacaa actagcaaaa   3240

taggctgtcc ccagtgcaag tgcaggtgcc agaacatttc tct                     3283
```

CELL BASED ASSAY

Filed even date herewith via the EFS-Web is an ASCII text file containing the sequence listing, which is named "MDL_00066_sequence_listing_ST25", was created on Mar. 10, 2017, and contains 9 kilobytes; said ASCII text file is incorporated herein by reference.

FIELD OF THE INVENTION

The present invention generally relates to cell-based assays involving HER2 and HER2 protein. These cell-based assays are used to measure the effect of mutations on the activity of HER2 protein and on their responses to inhibitors.

BACKGROUND OF THE INVENTION

HER2 protein is a member of the human epidermal growth factor receptor family. There are four members of this family which are plasma membrane bound receptor tyrosine kinases. Breast cancer is the most prevalent cancer in women, and about 25% of cases show HER2 gene amplification. Breast cancers with HER2 gene amplification or HER2 protein overexpression are typically referred to as HER2-positive in pathology reports. HER2-positive breast cancers tend to grow faster and are more likely to spread and recur compared to HER2-negative breast cancers. HER2 amplification is a major therapeutic target in breast cancer. There are medicines specifically for HER2-positive breast cancers. Lapatinib, which is an orally active drug approved for breast cancer treatment, is a dual tyrosine kinase inhibitor which targets both HER1 and HER2 tyrosine kinase activity. Two therapeutic antibodies, including Trastuzumab and Pertuzumab, targeting HER2 receptor are also approved by the FDA for breast cancer patients.

Cancer evolution and progression are driven by a sequence of somatic genetic and nongenetic alterations resulting in more favorable tumor cell growth and survival. Cancer genetic evolution is subject to intrinsic influences such as the tumor microenvironment, as well as extrinsic pressures such as drug therapy. The clinical pattern of acquired resistance may, in many circumstances, represent outgrowth of resistant clones, which may have originally been present in the cancer at low frequency as a result of intratumoral genetic heterogeneity, but grow out under the selective pressure of targeted therapy.

Advances in high-throughput sequencing technologies are beginning to establish a molecular taxonomy for a spectrum of human disease and have facilitated a move toward precision medicine. With regard to oncology, defining the mutational landscape of a patient's tumor will lead to more precise treatment and management of individuals with cancer. In addition to the potential for identifying 'actionable' therapeutic targets in cancer patients, the clinical sequencing may also shed light on acquired resistance mechanisms developed against targeted therapies. Although uncovering the DNA sequences of tumors becomes possible with the advances in next generation of sequencing ("NGS"), this technology does not provide any functional information of the identified mutations. Therefore, there is a need to develop a novel method to study the functional consequence of mutation(s) on the target gene activity and its response toward the drug treatment. This functional information will provide additional valuable guidelines for the physician to choose the most appropriate treatment based on the mutational landscape of a patient's tumor.

Accordingly, there is a continuing need to develop an improved clinical test using a cell-based assay that measures HER2 activity useful in assessing the effect of somatic HER2 gene mutations in the respective protein activity, as well as determining the sensitivity of HER2 variants to inhibitors.

SUMMARY OF THE INVENTION

In one aspect the present invention concerns a method of determining whether an HER2 variant is sensitive to treatment with an HER2 inhibitor in a cell, comprising the steps of:

a) preparing a cDNA encoding said HER2 variant;
b) preparing an expression cassette containing the HER2 variant cDNA;
c) transfecting said prepared expression cassette containing said HER2 variant cDNA in an assay cell having a JNK reporter construct comprising a reporter gene cDNA linked to at least one AP-1 binding site, and said cell is capable of expressing HER3;
d) exposing said transfected cell to a HER3 ligand, wherein HER3 complexes with said HER2 variant to form a dimer which thereby activates the JNK reporter construct and generates a signal;
e) exposing said transfected cell with an HER2 inhibitor; and
f) determining whether said HER2 variant is sensitive to treatment with said HER2 inhibitor by measuring a change in signal.

In another aspect the present invention concerns a method of determining the activity of a HER2 variant, comprising the steps of:

a) preparing a cDNA encoding said HER2 variant;
b) preparing an expression cassette containing the HER2 variant cDNA;
c) transfecting said prepared expression cassette containing said HER2 variant cDNA in a cell having a JNK reporter construct comprising a reporter gene cDNA linked to at least one AP-1 binding site, and said cell is capable of expressing HER3;
d) exposing said transfected cell to a HER3 ligand, wherein said HER3 complexes with said HER2 variant to form a dimer which thereby activates the JNK reporter construct and generates a signal;
e) determining the signal activity, wherein a change in signal activity relative to wild type HER2 is indicative of a change in activity of said HER2 variant.

DETAILED DESCRIPTION OF THE INVENTION

Figure 1:
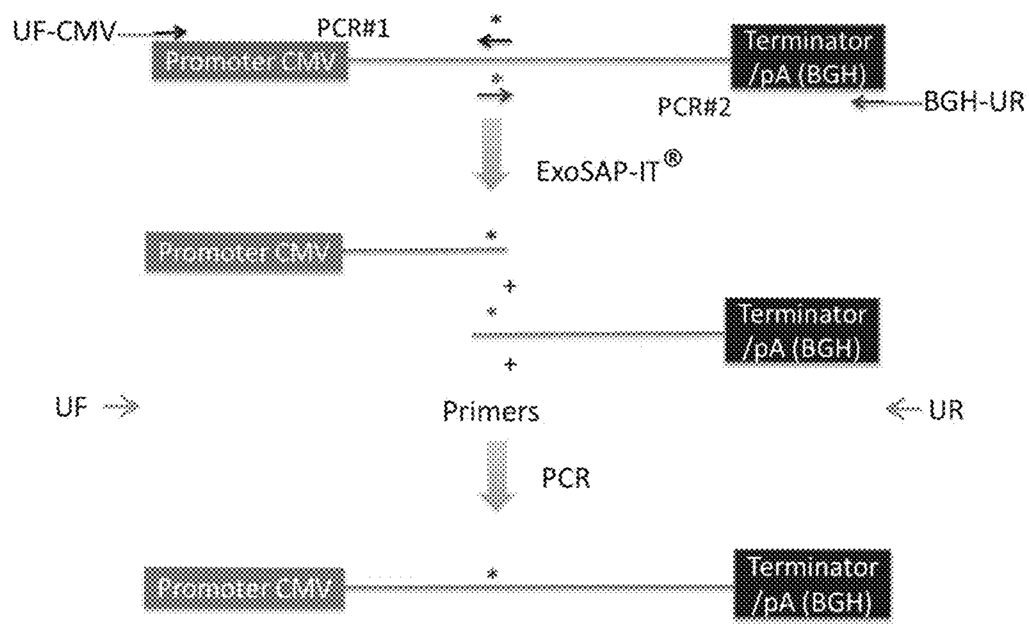
FIG. 1 depicts the PCR mediated overlapping extension to construct patient HER2 gene. Two rounds of PCR were performed. The first round of PCR included two independent PCR as illustrated as PCR#1 and PCR#2. HER2 expression plasmid was used as DNA template. Second round of PCR was performed after ExoSAP-IT® treatment. Mixture of the PCR products from first round of PCR was used as DNA template. The mutation was incorporated into the final linear expression cassette, which contained CMV promoter and BGH terminator, as illustrated in the figure.

The present invention can be better understood from the following description of preferred embodiments, taken in conjunction with the accompanying drawings. It should be apparent to those skilled in the art that the described embodiments of the present invention provided herein are merely exemplary and illustrative and not limiting. Numerous embodiments or modifications thereof are contemplated as falling within the scope of the present invention and equivalents thereto. All publications, patent applications, patents, and other references mentioned herein are incorporated by reference in their entirety.

In the context of the invention, the term "treating" or "treatment", as used herein, means reversing, alleviating, mitigating or inhibiting the progress of the disorder or condition to which such term applies, or one or more symptoms of such disorder or condition. As used herein and in the appended claims, the singular forms "a", "an", and "the" include plural reference unless the context clearly dictates otherwise.

Definitions

Various terms used in this specification shall have the definitions set out herein. All derivatives, inflections and conjugations or other grammatical forms of a specific term are intended to be included in the recited definition.

As used herein, the term "A," "T," "C", and "G" refer to adenine, thymine, cytosine, and guanine as a nucleotide base, respectively.

As used herein, the term "AP-1" refers to activator protein 1 which is a transcription factor activated by JNK proteins which has the sequence TGAGTCAG. AP-1 is capable of modulating gene expression in response to binding of certain ligands to HER cell surface receptors. Receptor occupancy triggers a signal transduction cascade to the nucleus. In this pathway or cascade, transcription factors such as AP-1 execute long term responses to the extracellular factors by modulating gene expression.

As used herein the term "HER" is a receptor protein tyrosine kinase which belongs to the HER receptor family and includes EGFR (ErbB1, HER1), HER2 (ErbB2), HER3 (ErbB3) and HER4 (ErbB4) receptors. The HER receptor will generally comprise an extracellular domain, which may bind an HER ligand and/or dimerize with another HER receptor molecule; a lipophilic transmembrane domain; a conserved intracellular tyrosine kinase domain; and a carboxyl-terminal signaling domain harboring several tyrosine residues which can be phosphorylated.

As used herein, the term "HER2" (also known as receptor tyrosine-protein kinase erbB-2 or ERBB2) refers to human epidermal growth factor receptor 2 which is encoded by HER2 having reference number NM_004448 in the National Center for Biotechnology Information ("NCBI") database.

As used herein, the term "HER1" refers to human epidermal growth factor receptor 2 which is encoded by HER1 having NCBI reference number NM_005228.

As used herein, the term "HER3" refers to human epidermal growth factor receptor 3 which is encoded by HER3 having NCBI reference number NM_001982.

As used herein the term "wild type" or "WT" means the typical form of an organism, strain, gene or characteristic as it occurs in nature as distinguished from mutant, variant, or modified forms.

As used herein the term "variant" means the exhibition of qualities that have a pattern that deviates from what occurs in nature or is distinct from the predominant form that occurs in nature.

As used herein, the term "vehicle" refers to the solvent of a compound.

As used herein, the term "CRISPR" refers to Clustered regularly interspaced short palindromic repeats, which are sequences used by CRISPR associated proteins (Cas) for the purpose of recognizing and cutting genetic elements. CRISPR/Cas9 uses sgRNA as a recognition sequence for identifying where the Cas9 will bind and cut the genetic element.

As used herein, the term "cancer" refers to a malignant neoplastic disease. Most cancers are characterized by hyperproliferation of a cell population.

As referred to herein, the term "assay cell" refers to a cell which is transfected for use in the assays of the invention.

As used herein, the term "tumor cell" or "cancer cell" refers to a malignant neoplastic cell.

As used herein, the term "luciferase activity" refers to the use of a luciferase protein or reporter to assess the amount of luciferase light emission. The activity is measured by addition of a substrate that binds to the luciferase protein and emits a light signal that can be measured using a luminometer.

As used herein, the term "promoter" refers to a region of the DNA that regulates the transcription of a particular gene.

As used herein, "expression" or "expressed" refers to the processes by which a polynucleotide is transcribed from a DNA template (such as into and mRNA or other RNA transcript) and further processed or translated into peptides, polypeptides, or proteins. Transcripts and encoded polypeptides may be collectively referred to as "gene product." If the polynucleotide is derived from genomic DNA, expression may include differential splicing of the mRNA in a eukaryotic cell leading to different forms of peptides or protein products.

As used herein, the term "construct" refers to a plasmid or polynucleotide, e.g., a linear cassette, containing cDNA to encode for a given protein. Constructs typically have the necessary components to express the desired protein encoded by the cDNA.

As used herein, the terms "stable expression" or "stably expressing" refer to the a cell line or group of cells that express a given protein for a period greater than 1 week, normally resulting in permanent expression of that protein over months.

As used herein, the term "stable cell" or "stable cell system" refers to the generation of cells using a selection method that specifically stably express a given protein. "Stable cell clone" is derived from a single cell with stable expression of a given protein.

As used herein, the term "transfection" refers to the process of introducing a polynucleotide into a cell, and more specifically into the interior of a membrane-enclosed space of a target cell(s), such as the cytosol of a cell, the nucleus of a cell, an interior space of a mitochondria, endoplasmic reticulum (ER), and the like. Transfection can be accomplished by any means known to those of skill in the art, for example as taught by Sambrook et al. Molecular Cloning: A Laboratory Manual, Cold Spring Harbor Laboratory Press, New York (2001), the contents of which are incorporated by reference herein. Examples of transfection techniques include, but are not limited to: heat shock, calcium phosphate transfection, PEI transfection, electroporation, lipofection, transfection reagent(s), viral-mediated transfer, and the like, or combinations thereof.

As used herein, the term "transiently transfected" refers to a cell that has been subject to a process of introducing a polynucleotide into a cell resulting in expression of a protein over a period from 12 hours to 7 days.

As used herein, the term "HER2 inhibitor" refers to a compound which targets and binds to HER2 or otherwise interacts directly or indirectly with HER2, which interferes with HER activation or function resulting in prevention or reduction of HER activity.

As used herein the term "HER3 ligand" refers to a compound, e.g., a polypeptide, which binds to and/or activates the HER3 receptor.

As used herein the term "HER2 activity" refers to the ability of HER2 to interact with other HER receptors to form heterodimers to induce downstream signaling activity.

As used herein the term "reporter" means a protein that when expressed in a cell is capable of producing a detectable signal.

As used herein the term "reporter gene" refers to a polynucleotide that encodes a reporter.

As used herein the term "JNK reporter construct" refers to a polynucleotide that contains cDNA encoding a reporter protein, typically an enzyme such as luciferase, and at least one copy of AP-1. An example of a JNK reporter construct is SEQ ID NO: 31.

As used herein the term "HER activation" refers to activation, or phosphorylation, of any one or more HER receptors.

As used herein the term "JNK protein" refers to a member of the JNK family of kinases, including but not limited to Jun N-terminal kinase 1 ("JNK1"), Jun N-terminal kinase 2 ("JNK2") and Jun-N-terminal kinase 3 ("JNK3"), their isoforms and other members of the JNK family of proteins that phosphorylate the amino terminal (N-terminal) portion of the Jun subunit of AP-1.

As used herein the term "dead" form of HER2 or HER2 refers to HER2 receptor containing a missense mutation at amino acid position 753. This mutation changes lysine to methionine, which results in inactivation of kinase activity of HER2 receptor In a typical situation a cell converts an extracellular signal or stimulus into a response, typically involving ordered sequences of biochemical reactions inside the cell. The phosphorylation of proteins plays a key role in the transduction of extracellular signals into the cell. Certain cell signaling pathways involve mitogen activated protein kinases, the so-called MAP (mitogen activated protein) kinases or MAPK. One of the MAPK-dependent pathways enables the transmission of signals from extracellular signals, such as neuregulin 1 or NRG1 which binds to a corresponding receptor in the cell membrane, i.e., the HER2/HER3 dimer, which sends the signal on to the cell nucleus via intermediary kinases and kinase targets (e.g., the MAPK pathway). Latter proteins in this pathway are JNK proteins which ultimately govern expression of genes that control vital cell functions such as proliferation, growth, motility and survival. JNK proteins are responsible for the phosphorylation of specific sites (Serine 63 and Serine 73) on the amino terminal portion of c-Jun. Phosphorylation of these sites potentiates the ability of AP-1 to activate gene expression.

The epidermal growth factor receptor family includes four transmembrane tyrosine kinase receptors named HER1, HER2, HER3 and HER4. HER receptors share a highly conserved extracellular domain, a transmembrane junction, and an intracellular ATP-binding kinase domain. Several ligands have been described to bind with different specificities to the extracellular domain of the HER receptors. Upon ligand binding, HER receptors form dimers that, following transphosphorylation of their kinase domains, recruit adaptor molecules responsible for the initiation of several signaling pathways involved in cell proliferation and survival. Although different dimer combinations of the four receptors are possible, the HER1/HER2 and HER2/HER3 heterodimers are considered the most potent and oncogenic combination. Therefore, it is desirable to characterize the expression of HER1, HER2 and HER3 in assay cells, e.g., transfected HEK293, MCF7, HeLa cells, and the like. If there are detectable amounts of these receptors in the assay cells in one embodiment the endogenous genes can be knocked out to eliminate potential interference with the assay.

CRISPR/Cas9 can be used to generate knock-out ("KO") cells by co-expressing a gRNA specific to the gene to be targeted and the endonuclease Cas9. An assay cell with two genes knocked out is referred to as a double knock-out or "DKO." The genomic target can be any 20 nucleotide DNA sequence, provided it meets two conditions:

1. The sequence is unique compared to the rest of the genome.
2. The target is present immediately upstream of a Protospacer Adjacent Motif ("PAM").

The PAM sequence is necessary for the target in order to provide specificity. Cas9 is the endonuclease from the species of *Streptococcus pyogenes*. Once expressed, the Cas9 protein and the gRNA form a riboprotein complex through interactions between the gRNA "scaffold" domain and surface-exposed positively-charged grooves on Cas9. Cas9 undergoes a conformational change upon gRNA binding that shifts the molecule from an inactive, non-DNA binding conformation, into an active DNA-binding conformation. The Cas9-gRNA complex will bind any genomic sequence with a PAM, but the extent to which the gRNA spacer matches the target DNA determines whether Cas9 will cut. Once the Cas9-gRNA complex binds a putative DNA target, a "seed" sequence at the 3' end of the gRNA targeting sequence begins to anneal to the target DNA. If the seed and target DNA sequences match, the gRNA will continue to anneal to the target DNA in a 3' to 5' direction. Cas9 will only cleave the target if sufficient homology exists between the gRNA spacer and target sequences. The Cas9 nuclease has two functional endonuclease domains: RuvC and HNH. Cas9 undergoes a second conformational change upon target binding that positions the nuclease domains to cleave opposite strands of the target DNA. The end result of Cas9-mediated DNA cleavage is a double strand break ("DSB") within the target DNA (3-4 nucleotides upstream of the PAM sequence). The resulting DSB is then repaired by one of two general repair pathways:

1: The efficient but error-prone Non-Homologous End Joining ("NHEJ") pathway

2: The less efficient but high-fidelity Homology Directed Repair ("HDR") pathway The NHEJ repair pathway is the most active repair mechanism, capable of rapidly repairing DSBs, but frequently results in small nucleotide insertions or deletions ("InDels") at the DSB site. In most cases, NHEJ gives rise to small InDels in the target DNA which result in in-frame amino acid deletions, insertions, or frameshift mutations leading to premature stop codons within the open reading frame ("ORF") of the targeted gene. Ideally, the end result is a loss-of-function mutation within the targeted gene; however, the "strength" of the knock-out phenotype for a given mutant cell is ultimately determined by the amount of residual gene function.

The HER family proteins are type I transmembrane growth factor receptors that function to activate intracellular signaling pathways in response to extracellular signals. Their structure consists of an extracellular ligand binding domain, a transmembrane domain, and an intracellular tyrosine kinase domain. The extracellular domain of HER proteins can exist in a closed inhibited or an open active conformation. Ligand binding causes a conformational change in their extracellular domain that induces the active conformation and promotes their dimerization and consequent transphosphorylation. Partner selection appears to be a key determinant of signaling activity among HER proteins and their signaling functions follow a distinct hierarchical order favoring heterodimers over homodimers. HER2 has the strongest catalytic kinase activity and HER2-containing heterodimers have the strongest signaling functions. Unlike the other members of the family, HER2 lacks ligand binding activity and its signaling function is engaged by its ligand-bound heterodimeric partners.

Unlike the other members of the family, the extracellular domain of HER2 does not pivot between active and inactive conformations and constitutively exists in an activated conformation. Consistent with its constitutively active conformation, HER2 lacks ligand binding activity and its signaling function is engaged by its ligand-bound heterodimeric partners. On the other hand HER3, unlike the other members, lacks ATP binding within its catalytic domain and is catalytically inactive. Consistent with this, the signaling functions of HER3 are mediated entirely through the kinase activity of its heterodimeric partners. Although individually they are incomplete signaling molecules, a large body of evidence not only establishes HER2 and HER3 as obligate partners but their complex forms the most active signaling heterodimer of the family and essential for many biologic and developmental processes. HER1 contains both ligand binding activity and its cytosolic catalytic kinase domain. HER1 can form homodimer or/and heterodimer to engage its signaling function.

In general, there are two major types of transfection, forward and reverse. The most routinely employed transfection protocol where cells are seeded a day prior to transfection is referred to as "forward transfection". Forward transfection methods work well for most adherent cell types that are seeded a day prior to transfection in order to achieve an actively dividing cell population at the time of transfection. A "reverse transfection" protocol where freshly passaged cells are added to transfection complexes has the advantage of reducing hands-on time for the end user. In this scenario, cells are not adhered to the plate surface by the time they interact with the transfection complexes.

The present invention relates to HER2 variants sensitivity to treatment, HER2 variants sensitivity to inhibitors and whether compounds inhibit HER2 activity in a cell. In one aspect, the present invention provides highly sensitive methods for determining whether a HER2 variant is sensitive to treatment using a HER2 inhibitor.

Methods include providing a cell system containing cDNA constructs with signaling capability to measure the activity of HER2 variants and the variants response to treatment with inhibitors. The HER2 variants may include one or more mutations in the respective gene. Identification of the HER2 variants may be obtained from sequencing of a biological sample or produced using, e.g., Next Generation Sequencing (NGS).

The assay cells of the invention are transfected with a reporter gene containing one or more AP-1 binding sites. The assay cells can be either transiently or stably transfected with the JNK reporter construct. In a particular embodiment the assay cells contain a stably integrated JNK reporter construct. When formation of HER2/HER3 dimer is induced by a HER3 ligand, a biochemical signaling cascade involving various kinases activates the expression of reporter gene which results in production of a signal. In some embodiments in order to produce a signal a substrate must be provided for the reporter. The signal can be, for example, a light signal. In some embodiments the reporter is an enzyme which can be any protein produced from any gene that exhibits enzymatic activity and degrades a substrate to produce a light or luminescence signal. The light signal can be measured using a luminometer. In certain embodiments, the light is measured by fluorescence signaling systems such as Fluorescence Resonance Energy Transfer (FRET).

Examples of reporter enzymes include luciferase, alkaline phosphatase, chloramphenicol transferase, β-galactosidase, β-glucuronidase, carboxylesterase, lipases, phospholipases, sulphatases, ureases peptidases, proteases and the like. In a particular embodiment the reporter is luciferase, for example, firefly luciferase, Renilla luciferase, and the like. In one aspect, the present invention provides a method to determine HER2 gene activity using a cell based reporter assay. Ligand-dependent nuclear transactivation involves activation of the JNK pathway. In the assays of the invention the stable assay cells contain a reporter construct which comprises a reporter gene containing AP-1 binding sites. Binding of a HER3 ligand to the HER2/HER3 dimer results in a signal. In one embodiment HER3 ligand binding induces expression of the reporter which leads to generation of light emission when a substrate is added, and therefore allows for indirect measurement of HER2 activity. Typical substrates for luciferase include D-luciferin and salts thereof.

The present assay can be used in personalized medicine. When genome information is obtained relating to the HER2 or HER2 sequences, one skilled in the art can conveniently prepare a cDNA based on the HER2 gene sequence information. The generated cDNA therefore contains a unique cDNA for that individual because it contains a gene sequence of the specific gene of that individual. The HER2 construct containing either the variant or WT HER2 can be transfected into the assay cell via either a plasmid or linear expression cassette. In certain embodiments, the cDNA encoding the HER2 variant may be transiently transfected into the cell. One advantage of a preferred assay of the invention is to transfect the generated HER2 cDNA into an assay cell with a linear cassette. Compressing or shortening the time required to perform the assays of the invention can be important when performing the assays in a clinical laboratory. By use of linear cassette transfection the time required to obtain and report results to a physician can be substantially shortened relative to prior art methods using plasmids. For example performing the assays of the invention (i.e., steps (a) through (f) of the inhibitor sensitivity assays, and steps (a) through (e) of the activity assays) can take 32 hours or less, typically 30 hours or less, preferably 28 hours or less.

Normally, transfection with the linear cassette takes about 4 to 24 hours, in some embodiments about 5 to 20 hours, in another embodiment about 6 to 12 hours. In one embodiment, once the assay cells are transfected with the HER2 cassette, the assay cells are cultured or incubated under conditions suitable for adequate cell growth and expression of the proteins of interest; in one embodiment the conditions include a culture time of 24 to 48 hours typically at about 37° C. After transfection, the assay cells are exposed to a HER3 ligand for about 2 to 6 hours. If a HER2 inhibitor is used in the assay, the assay cells are exposed to said inhibitor for about 2 to 6 hours. In a certain embodiment, contacting or exposure with inhibitor is performed after incubating the assay cells with a HER ligand inducing HER dimerization.

The HER ligand can be any compound that binds to or interacts with HER3 and activates the receptor. HER ligands can be polypeptides. The HER ligand can be an antibody or fragment thereof, alpha, beta and gamma heregulins; neuregulin-1 ("NRG1"), neuregulion-2, neuregulin-3, neuregulin-4, and the like.

The ligand and inhibitor in one embodiment are added to the assay cells at about the same time, i.e., simultaneously. In another embodiment, it has been surprisingly discovered that ligand can be added at about the same time as transfection with the HER2 cassette, i.e., performing steps c) and d) simultaneously (termed herein as the "all-in-one" method), and still result in a good dose response to the respective ligand.

Transfection with the linear expression cassette can be a "forward transfection" or a "reverse transfection." Forward transfection is where cells are seeded a day prior to transfection in order to achieve an actively dividing cell population adhered to a vessel surface at the time of transfection. Reverse transfection is where freshly passaged cells are added to transfection complexes. Reverse transfection has the advantage of reducing the time for performing assays; however, because the cells are not adhered to the surface of the assay vessel (e.g., surface of the wells of the assay plate) and are not in a robust growth phase, reverse transfection can be unsuitable for certain assays. It has been discovered that for the assays of the invention reverse transfection results in satisfactory signal production, in particular luciferase production, in the assay cells.

In certain embodiments, the assay cell is transfected with a cDNA containing HER2 gene of interest, typically a variant. The cDNA can be conveniently prepared using standard methodologies known to one skilled in the art. In certain embodiments, the cDNA can encode HER2 wild type. In certain embodiments the cDNA can encode a HER2 variant. In further embodiments, the variants can contain one or more mutations different from the HER2 wild type. The HER2 construct containing either the variant or WT HER2 can be either in a plasmid or linear expression cassette format. In certain embodiments, the HER2 variant contains one mutation. In certain embodiments, the specific variant may contain two mutations. In certain embodiments, the variant may contain three mutations. In certain embodiments the variant may contain four or more mutations.

In some embodiments, the HER2 variant contains a missense mutation, insertion, or deletion. Examples of missense mutations in HER2 are T862A, L755S, and the like. An example of an insertion for HER2 is P780ins.

In addition to the HER2 cDNA encoding a variant, the expression cassette, preferably linear, also comprises other components necessary or desirable for effective expression. These components may vary depending on the particular assay cell chosen. Such other components typically include a promoter and terminator. Promoters include the cytomegalovirus (CMV) promoter, the SV40 promoter, elongation factor (EF)-1 promoter and the like. Typical terminators are SV40; hGH, BGH, and rbGlob. In addition a polyadenylation or poly(A) signal sequence is typically included. The assay cells can be either stably or transiently transfected with the HER2 expression cassette, but it typically is transiently transfected.

In some embodiments the assays cells are stably transfected with JNK reporter constructs. Stable transfection has the advantage of passing the DNA to the progeny of the cells. Stable transfection typically incorporates the transfected DNA into the genome of the assay cell, but it is possible that transfected DNA can be stable even though not incorporated into the genome. In some embodiments the assay cells are transfected with JNK reporter constructs that have multiple copies of AP-1 binding sites, e.g., 2, 3, 4, 5, 6, 9, 12 or more copies. In one embodiment the reporter construct has 6 or more AP-1 binding sites, in a particular embodiment the signal expression construct has 6 AP-1 binding sites. Usually multiple copies of AP-1 result in enhanced generation of signal. The introduced reporter construct is preferably integrated into the host genome and retained in the cells even after assay cells replicate. The JNK reporter constructs also comprises other components necessary or desirable for effective stable transfection, similar to the HER2 and HER3 constructs. These components may vary depending on the particular host or parent cell chosen. In addition to components such as a promoter, terminator and polyA sequence, such other components can include, for example, a marker gene for selecting and identifying cells containing the reporter constructs integrated into the host genome. Such marker gene can be, for example, genes that encode a fluorescent protein or encode antibiotic resistance such as resistance to hygomycin B, neomycin, puromycin and the like. The marker gene can be part of the signal expression construct or can be part of a separate construct co-transfected with the signal expression construct.

The assay cells of the invention are capable of expressing HER3. The expression of HER3 is important in order for the expressed HER3 to dimerize with HER2 expressed for the transfected HER2 cDNA. If the particular assay cell chosen expresses sufficient endogenous HER3, then endogenously expressed HER3 may be sufficient. However, if endogenous HER3 expression is low or absent, then it may be desirable to transfect the assay cell with an additional construct containing HER3 cDNA. Such a HER3 construct will comprises other components necessary or desirable for effective transfection. These components may vary depending on the particular assay cell chosen. Such other components typically include a promoter, terminator and poly A sequences as described above. The HER3 construct can contain multiple copies of the HER3 gene. The assay cell can be either stably or transiently transfected with the HER3 expression construct, but it is preferably stably transfected.

The assay cells of the invention can be transfected with the constructs described herein individually via a plasmid or linear expression cassette or the desired genes can be part of the same plasmid or linear expression cassette. For example, in one embodiment both the JNK reporter construct and the HER3 construct are contained in the same plasmid or linear expression construct. In another embodiment both the JNK reporter and HER3 are in two separated plasmids and they are both stably integrated into the genome.

In another aspect, the present invention provides a method to determine whether a particular HER2 variant is sensitive to treatment with a HER2 inhibitor in a cell. The method involves preparing a cDNA containing a HER2 variant of interest followed by transfecting the cDNA into an assay cell. In certain embodiments, the transfected cells are then exposed to an inhibitor. HER 2 inhibitors include, without limitation, HER antibodies and antibody fragments, small molecule HER2 antagonists, HER2 tyrosine kinases inhibitors, and antisense molecules. In one embodiment, the HER2 inhibitor is a HER2 antibody or antibody fragment, or a small molecule, which binds to and inhibits the HER2 receptor. In various embodiments, the HER2 antibody may inhibits HER2 ectodomain cleavage, may block ligand activation of a HER receptor, or may inhibit HER2 dimerization.

Known HER2 inhibitors are tyrosine kinase inhibitors (Lapatinib) and monoclonal antibodies (Trastuzumab and Pertuzumab). HER2 receptor is a transmembrane receptor; it has an extracellular binding component, a transmembrane component and an intracellular tyrosine kinase component. Tyrosine kinase inhibitors bind to the tyrosine kinase domain in the HER2 and stops activation of the signaling pathway. Monoclonal antibodies bind to the extracellular component of the HER2 and stop the receptor activation.

A convenient approach is to obtain a concentration dependent response for an inhibitor by performing a dose dependent curve study. By way of example, Lapatinib can be used from about 0.01 nM to about 10 nM, in one embodiment from about 0.05 nM to about 5 nM, in another embodiment from about 0.1 nM to about 1 nM. The other inhibitors can be used at the same concentrations as Lapatinib or modified as appropriate. The sensitivity of the HER2 variant toward a particular inhibitor can be conveniently measured by an increasing light emission as compared to a negative control (i.e., an assay cell exposed to vehicle alone without the inhibitor).

In certain embodiments, the cells express a knock down or knockout of endogenous HER 1, HER2 and/or HER3. In a particular embodiment the assay cells have a DKO of HER1 and HER2. In certain embodiments, the knock down is a genomic modification of at least a portion of the desired HER gene. In certain embodiments, the genomic modification is performed using CRISPR-CAS9 technology. In certain embodiments, the genomic modification is performed using TALENs or recombination technology.

In one aspect, the present invention provides an assay to test patient variants of the HER2 gene, preferably as identified by next generation sequencing (NGS), thus determining potentially hyperactive and/or inhibitor resistant mutations. When cells are treated with a HER2 inhibitor and HER2 is inhibited, activation of the JNK signaling pathway is prevented which results in decreasing the growth and replication of the cell, thereby inhibiting cancer cells.

In certain embodiments, the present assay may be used to determine whether a patient HER2 variant will respond to a specific inhibitor. The specific variant is determined from a patient's biological sample. The method involves preparing a cDNA containing a HER2 variant from a patient followed by transfecting the cDNA into a cell. Depending upon the particular cell line and other conditions, if any endogenous HER2 can be produced by the assay cells, the cells can undergo a genomic modification for gene deletion (knockout) or knockdown to reduce or prevent interference with the assays of the invention. In another embodiment, if the assay cells do not express the endogenous HER2 gene, then no such genomic modification will be needed. It also may be desirable to knockout or knockdown other HER receptors to improve assay interference, e.g., HER1. After determining the activity of the HER2 variant of a patient, the physician can use this information to adjust therapy. Appropriate therapy may include surgery, radiation, chemotherapy, immunotherapy, hormone therapy, targeted therapy, and the like. For example, if the HER2 variant is constitutively active and its activity is independent of ligand, then HER2 inhibitors should not be used. If the HER2 variant activity depends on ligand, then HER2 inhibitors should be used.

In some embodiments, the biological sample is from patients selected from: blood, serum, and tumor tissue. The biological sample can be tissue or cells from a breast tumor. In some embodiments, the biological sample may be freshly isolated. In some embodiments, the biological sample may be frozen. In some embodiments, the biological sample may be fixed. The biological sample can be processed to obtain HER2 genomic information and the HER2 variants can be sequenced using know techniques, e.g., NGS. The genomic information can then be used to generate polynucleotides that can then be used to transfect the assay cells. In an alternate embodiment, the HER2 polynucleotides can be isolated directly from the biological sample and used to transfect the assay cells.

Sample preparation includes isolation of nucleic acids (e.g., DNA, mRNA). These isolation procedures involve separation of nucleic acids from insoluble components (e.g., cytoskeleton) and cellular membranes. In one embodiment, biological tissues or cells are treated with a lysis buffer solution prior to isolation of nucleic acids. A lysis buffer solution is designed to lyse tissues, cells, lipids and other biomolecules potentially present in the raw tissue samples. Generally, a lysis buffer of the present invention may contain a chemical agent that includes one or more of the following ingredients: (i) chaotropic agents (e.g., urea, guanidine thiocyanide, or formamide); (ii) anionic detergents (e.g., SDS, N-lauryl sarcosine, sodium deoxycholate, olefine sulphates and sulphonates, alkyl isethionates, or sucrose esters); (iii) cationic detergents (e.g., cetyl trimethylammonium chloride); (iv) non-ionic detergents (e.g., Tween®-20, polyethylene glycol sorbitan monolaurate, nonidet P-40, Triton® X-100, NP-40, N-octyl-glucoside); (v) amphoteric detergents (e.g., CHAPS, 3-dodecyl-dimethylammonio-propane-1-sulfonate, lauryldimethylamine oxide); or (vi) alkali hydroxides (e.g., sodium hydroxide or potassium hydroxide). Suitable liquids that can solubilize the cellular components of biological samples are regarded as a lysis buffer for purposes of this application.

In another embodiment, a lysis buffer may contain additional substances to enhance the properties of the solvent in a lysis buffer (e.g., prevent degradation of nucleic acid components within the raw biological samples). Such components may include RNAse inhibitors, DNAse inhibitors, and the like. RNAse inhibitors include common commercially available inhibitors such as SUPERase.In™ (Ambion, Inc. Austin, Tx), RNAse Zap® (Ambion, Inc. Austin, Tx), Qiagen RNase inhibitor (Valencia, Calif.), and the like.

Nucleic acids, such as mRNA or DNA, can be conveniently extracted from biological samples using standard extraction methods that are known in the art. Standard extraction methods include the use of a chemical agent such as guanidinium thiocyanate, phenol-chloroform extraction, guanidine-based extraction, and the like. Commercial nucleic acid extraction kits may be employed. For example, RNeasy Fibrous Tissue Mini Kit from Qiagen (Valencia, Calif.) and RNAimage Kit from GenHunter Corporation (USA).

The technique of "polymerase chain reaction" or "PCR" as used herein generally refers to a procedure wherein minute amounts of a specific piece of nucleic acid, RNA and/or DNA, are amplified as described in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol., 51:263 (1987); Erlich, ed., PCR Technology, (Stockton Press, N Y, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

Any suitable sequencing method can be used according to the invention, Next Generation Sequencing (NGS) technologies being preferred. Third Generation Sequencing methods might substitute for the NGS technology in the future to speed up the sequencing step of the assay. For clarification purposes: the terms "Next Generation Sequencing" or "NGS" in the context of the present invention mean all novel high throughput sequencing technologies which, in contrast to the "conventional" sequencing methodology known as Sanger chemistry, read nucleic acid templates randomly in parallel along the entire genome by breaking the entire genome into small pieces. Such NGS technologies (also known as massively parallel sequencing technologies) are able to deliver nucleic acid sequence information of a whole genome, exome, transcriptome (all transcribed sequences of a genome) or methylome (all methylated sequences of a genome) in very short time periods, e.g. within 1-2 weeks, preferably within 1-7 days or most preferably within less than 24 hours and allow, in principle, single cell sequencing approaches. Multiple NGS platforms which are commercially available or which are mentioned in the literature can be used in the context of the present invention e.g. those described in detail in Zhang et al. 2011*: The impact of next-generation sequencing on genomics. J. Genet Genomics* 38 (3), 95-109; or in Voelkerding et al. 2009*: Next generation sequencing: From basic research to diagnostics. Clinical chemistry* 55, 641-658.

The assay cells of the invention are capable of expressing a reporter regulated by HER2. In some embodiments, the test cell is a eukaryotic cell. In some embodiments the assay cells are mammalian cells, such as rat, mouse, hamster, monkey and human cells. In some embodiments, the test cell may be a primary cell or a cell line. In another embodiment, an assay cell is a non-cancerous cell. In another embodiment, an assay cell is derived from a cell line. In another embodiment, an assay cell is amenable by transfection. In another embodiment, an assay cell is amenable by transient transfection. In another embodiment, an assay cell is a cell in which the expression of one or more endogenous genes have been reduced or eliminated by any molecular method. For example, in some embodiments it may be desirable to knockdown or knockout endogenous HER1 and/or HER2. Specific examples of cells useful in the assays of the invention (i.e., before modifying the cells with the constructs described herein, also known as "parent cells") include HEK293 (human embryo kidney), MCF-7 (human breast cancer), Hela (human cervix epithelial carcinoma), HT29 (human colon adenocarcinoma grade II), A431 (human squamous carcinoma), IMR 32 (human neuroblastoma), K562 (human chronic myelogenous leukemia), U937 (human histiocytic lymphoma), MDA-MB-231 (Human breast adenocarcinoma), SK-N-BE(2) (human neuroblastoma), SH-SY5Y (human neuroblastoma), HL60 (human promyelocytic leukemia), CHO (hamster Chinese ovary), COS-7 (monkey African green kidney, SV40 transformed), S49 (mouse lymphoma), Ltk (mouse C34/connective tissue), NG108-15 (mouse neuroblastoma×Rat glioma hybrid), B35 (rat nervous tissue neuronal), B50 (rat nervous tissue neuronal), B104 (rat nervous tissue neuronal), C6 (rat glial tumor), Jurkat (human leukemic T cell lymphoblast), BHK (hamster Syrian kidney), Neuro-2a (mouse albino neuroblastoma), NIH/3T3 (mouse embryo fibroblast), A549 (human adenocarcinoma alveolar epithelial), Be2C (human neuroblastoma), SW480 (human lymph node metastasis), Caco2 (human epithelial colorectal adenocarcinoma), THP1 (human acute monocyte leukemia), IMR90 (human lung fibroblast), HT1080 (human fibrosarcoma), LnCap (human prostate adenocarcinoma), HepG2 (human liver carcinoma) PC12 (rat pheochromocytoma), or SKBR3 (human breast cancer) cells. In another embodiment, an assay cell is U20S cell. In another embodiment, an assay cell is NCI60 cell lines, such as, A549, EKVX, T47D, HT29.

HEK 293 cells are a specific cell line originally derived from human embryonic kidney cells grown in tissue culture and are a preferred parent cell line. HEK 293 cells have been widely used in cell biology research for many years, because of their reliable growth and propensity for transfection.

In the assays using HER2 inhibitors, the inhibitors that are exposed to the assay cells are typically solubilized or suspended in a vehicle. A control is typically performed with vehicle without the inhibitor. Depending on the compound to be utilized as an inhibitor in the assay, suitable vehicles include dimethylsulfoxide ("DMSO"), dimethylformamide ("DMF"), water, aliphatic alcohols, and mixtures thereof.

According to some embodiments, there is provided a kit for determining HER2 activity in a patient or for determining a patient's response to HER2 inhibitors. In some embodiments, there is provided a kit for assessing patient specific mutations.

In some embodiments, the invention provides a kit for determining the molecular cancer profile in a subject, by identifying patient specific HER2 variants. In another embodiment, the kit comprises at least one means of detecting a reporter gene. In some embodiments, the kit contains one or more of: a substrate or container for holding nucleic acid molecules and/or test cells, directions for carrying out the assay(s), test cells, transfection reagents, or any combination thereof.

Compositions of the present invention may, if desired, be presented in an article of manufacture, which may contain diagnostic reagents and printed instructions for use. The kit may also be accommodated by a notice associated with the container in a form prescribed by a governmental agency regulating the manufacture, use or sale of assay products.

The assays are performed in a vessel capable of holding the cells and reagents and not interfering with assay results. In some embodiments the assay cells adhere to the surfaces of the vessel, e.g., the surfaces of assay plate wells. In some embodiments the assays are miniaturized and use multi-well plates known in the art. In certain embodiments, the present assay can be conveniently used in a 96 well plate, but can also be adopted for high throughput in 384 well plates or 1536 well plates. One skilled in the art will be able to easily optimize the well plates to suit throughput necessity. Plates for the assays are typically made of a polymer, e.g., polystyrene and the like. In some embodiments the plates are surface treated to facilitate adherence of the assay cells to the wells of the plate, such treatment is commonly referred to as "tissue culture treated". The surface treatment is typically an oxygen plasma discharge that renders the surface of the wells more hydrophilic. In some embodiments dispensing the cells and/or reagents for the assays into the wells of the plates is automated. In some embodiments the cells and/or reagents are dispensed continuously at a high speed. In one embodiment an acoustic liquid dispenser is used to dispense the reagents, e.g., HER2 inhibitors.

Any discussion of the content of references cited herein is intended merely to provide a general summary of assertions made by the authors of the references, and does not constitute an admission as to the accuracy of the content of such references. The following examples are provided to further illustrate various preferred embodiments and techniques of the invention. It should be understood, however, that these examples do not limit the scope of the invention described in the claims. Many variations and modifications are intended to be encompassed within the spirit and scope of the invention.

EXAMPLES

Example 1

Next-generation Sequencing to Interrogate Mutation of Tumor

Genetic change or mutation of genes is one of the mechanisms to acquire resistance in breast cancer during targeted therapy. To survey the mutation status of HER2 genes, whole-exome sequencing of the tumor was performed. Cancer tissue was isolated from formalin fixed paraffin embedded ("FFPE") blocks of tumor. Genomic DNA was extracted and was used to prepare a library for next-generation sequencing. The identified mutations, which caused changes in the amino acid sequence, were selected to examine their functional effect on the genes in the cell-based assay of the invention. The patient gene carrying the identified mutation is constructed using PCR mediated overlapping extension in a format of linear expression cassette.

Example 2

Construction of Linear Expression Cassette of Human HER2 Receptor

In order to study the effect of unknown mutations in human HER2 gene, linear expression cassettes were generated, which contained CMV promoter controlling expression of HER2 coding sequence followed by terminator and polyadenylation signal. To do so, overlapping extension PCR was employed to construct the linear expression cassette using an expression plasmid of human HER2 as PCR template. Using this method, the construction of a linear expression cassette takes around 4-8 hours. However, the traditional cloning method to generate an expression plasmid takes around 2-4 days. Therefore, making patient gene(s) in a linear expression cassette format is highly advantageous for a clinical diagnostic test because of its quick turn-around time.

Construction of Expression Plasmids of Human HER1, HER2 and HER3 cDNA plasmids containing human HER1, HER2 and HER3 genes were purchased (Dharmacon). The coding sequence of these genes was amplified by the PCR. NheI and XhoI restriction enzyme sites were inserted into forward and reverse primers respectively for the purpose of cloning of HER1 and HER2. NheI and XbaI restriction enzyme sites were inserted into forward and reverse primers respectively for the purpose of cloning of HER3. The PCR products containing the coding sequences of these human genes were sub-cloned into the pcDNA3.1 (+) using NheI and XbaI or XhoI restriction enzymes. The nucleotide sequences of human HER1, HER2 and HER3 were verified by DNA sequencing. The human HER2 expression plasmid was used as PCR template to construct the linear expression cassettes of wild-type HER2 or mutated forms of HER2. The expression plasmids of HER1 and HER3 were used in the identification and construction of a reporter system for HER2 assay.

Generation of Linear Expression Cassette of Human Normal and Mutated HER2

A linear expression cassette of human wild-type HER2 was generated by PCR using UF-CMV forward and BGH-UR reverse primers. The amplified products were gel-purified. The DNA concentration was quantitated by the optical density at 260 nm using a Nanodrop spectrophotometer.

A linear expression cassette of mutated HER2 was generated by a PCR mediated overlapping extension method. A pair of forward and reverse primers containing the targeted mutations was designed. The mutated codon (3 nucleotides) was located in the middle of a primer flanked by 18 nucleotides in each side. Two separate PCR procedures, named as PCR#1 and PCR#2 in FIG. 1, were performed using UF-CMV forward and mutated reverse primers, or mutated forward and BGH-UR primers. The PCR products were purified by ExoSAP-IT® (Affymetrix) to remove unconsumed dNTPs and primers. These two treated PCR products were mixed together followed by dilution with water. A second round of PCR was performed using the diluted PCR mixture as template, and UF and UR primers (FIG. 1). The amplified products were gel-purified. The DNA concentration was quantitated by the optical density at 260 nm using Nanodrop. The targeted mutations were incorporated in the HER2 gene using this PCR mediated overlapping extension method.

Example 3

Identification of Transfection Method

Comparison of Forward or Reverse Transfection Protocols

In order to test the possibility of using "reverse transfection" method to save time (typically about a day), a reporter plasmid, CDH1-luc, containing active CDH1 promoter was used. Since our clinical assay employed the linear expression cassette to express the patient ESR1 gene which contains a mutation found in the tumor, PCR was performed to generate a linear version of CDH1-luc. This linear reporter was gel-purified. The DNA concentration was quantitated by the optical density at 260 nm using Nanodrop.

Figure 2:
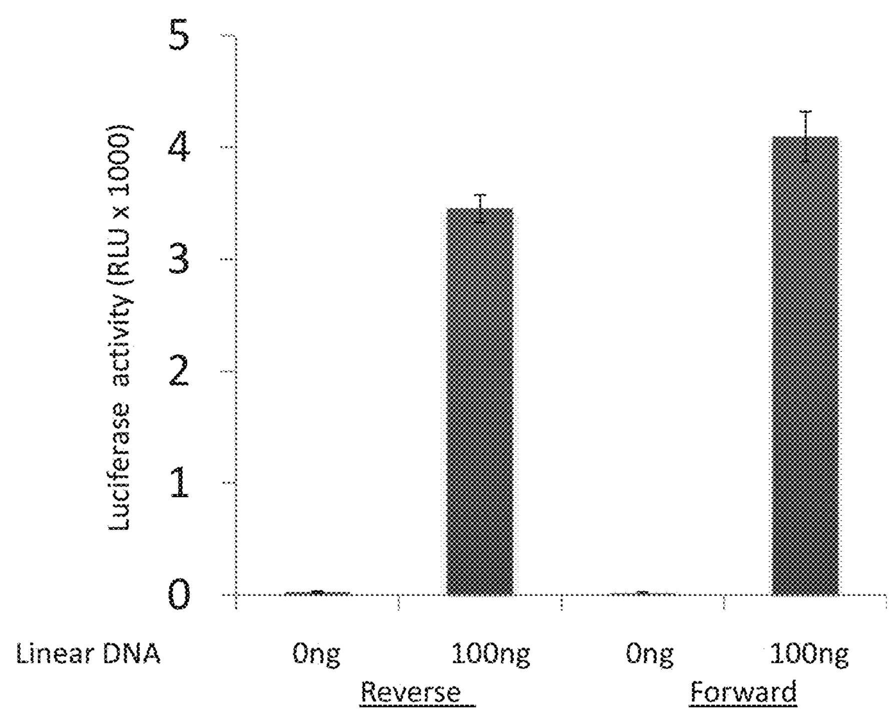
FIG. 2 depicts the luciferase reporter activity of HEK 293 cells transfected with active luciferase reporter using reverse and forward transfection methods.

To compare the "forward transfection" and "reverse transfection" protocols, HEK 293 cells were transiently transfected with 100 ng of purified linear reporter using TransIT-293 transfection reagent (Mirus Bio). This transfection reagent was optimized to give maximum transfection performance in HEK 293 cells. The transfection efficiency was measured by Nano-Glo® Luciferase assay (Promega) 24 hours post-transfection (FIG. 2). Significant luciferase activity was detected over the background signal using either forward or reverse transfection protocol. There is no substantial difference of luciferase signal between these two protocols. Therefore, these results demonstrated that a "reverse transfection" protocol can be used to transiently transfect linear DNA into HEK 293 cells.

Example 4

Generation of Double Knockout Cells—HER1 and HER2 Receptors

Expression of HER1, HER2 and HER3 in the HEK293 Cells

Figure 3:
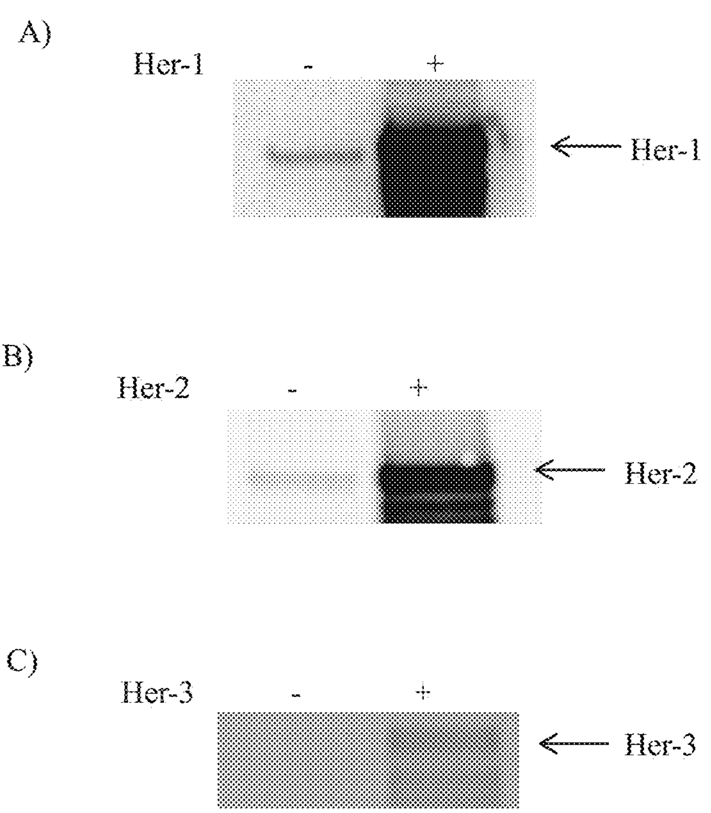
FIG. 3 depicts the immunoblot result using antibodies against A) HER1, B) HER2 and C) HER2 receptors. HEK 293 cells were transfected with nothing or expression plasmid of HER1, HER2 or HER3.

In order to examine the expression of HER1, HER2 and HER3 receptors, HEK293 cells were first transfected with pcDNA (as a negative control), or expression constructs of HER1, HER2 or HER3. Cellular lysates were prepared 48 hours after transfection. Immunoblots were performed using anti-Her1, anti-Her2 and anti-Her3 antibodies (FIG. 3). When the cells were transfected with the expression plasmids of these receptors, their expression were detected in all cases. When the cells were transfected with the control plasmid (pcDNA), endogenous HER1 and HER2 receptors were detected in the HEK293 cells but no HER3 receptor was detected. This result indicates that a preferred embodiment is to delete endogenous HER1 and HER2 receptors for the assay of the invention.

Knockout of HER2 by CRISPR Technology

In order to knockout the HER2 receptor in the genome of HEK293 cells, CRISPR knockout constructs designed specifically for human HER2 were obtained from Santa Cruz Biotechnology. The constructs containing gRNA sequences direct the Cas9 protein to induce a site-specific double strand break in the HER2 genomic region, which results in the deletion after repairing. To examine the deletion, primers flanking the gRNA targeting region were designed. These primers were used to perform genomic PCR to reveal the genomic status.

Figure 4:
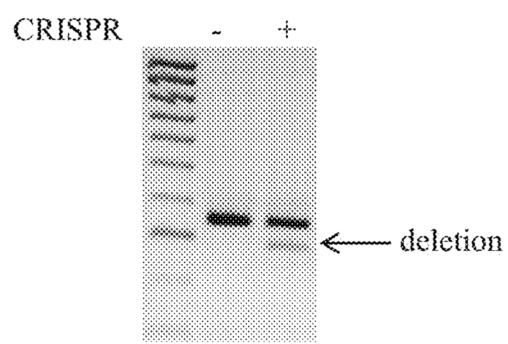
FIG. 4 depicts the result of genomic PCR screening of HER2 CRISPR knockout cells. A) HEK 293 cells were transiently transfected with the HER2 CRISPR constructs. B) Single cell clones of cells transfected with the HER2 CRISPR constructs.
Figure 4:
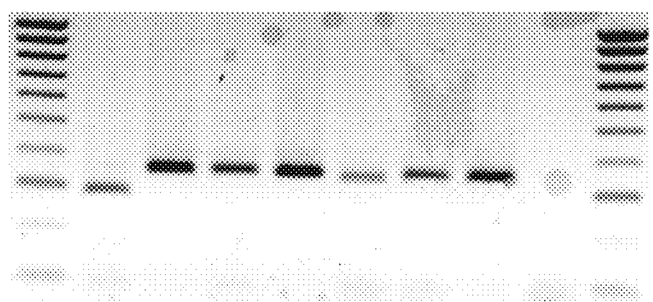

In transient transfection, HEK293 cells were transfected with the CRISPR constructs. Genomic DNA was prepared 48 hours after transfection. PCR was performed using the primers flanking the targeted area. In FIG. 4A, a smaller PCR band was detected in the cells transfected with CRISPR constructs. This result shows that these HER2 specific CRISPR constructs are capable of inducing double strand DNA break which results in deletion.

Figure 5:
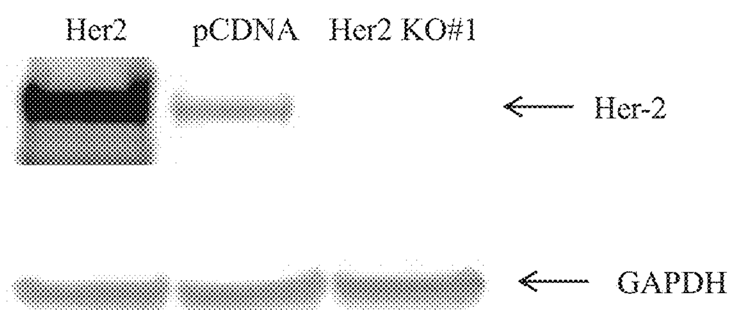
FIG. 5 depicts the immunoblot result of HER2 knockout cell clone using antibody against HER2 receptor. Antibody against GAPDH was used a loading control.

In order to generate stable knockout HER2 cells, the CRISPR constructs were transiently transfected into the HEK293 cells. The transfected cells were singly plated in 96-well plate 24 hours post-transfection. Seven single cells were chosen and expanded. Genomic DNA was prepared. PCR was performed using the primers flanking the targeted area. In FIG. 4B, clone #1 showed only the smaller PCR band, which indicated that it is potentially a homozygous HER2 knockout clone. To confirm the HER2 knockout status of clone #1, cellular extract was prepared. Immunoblot was performed using anti-Her2 antibody (FIG. 5). Expression of HER2 receptor was not detected in the clone #1. This result confirmed that clone #1 is a complete knockout of HER2 receptor.

Figure 6:
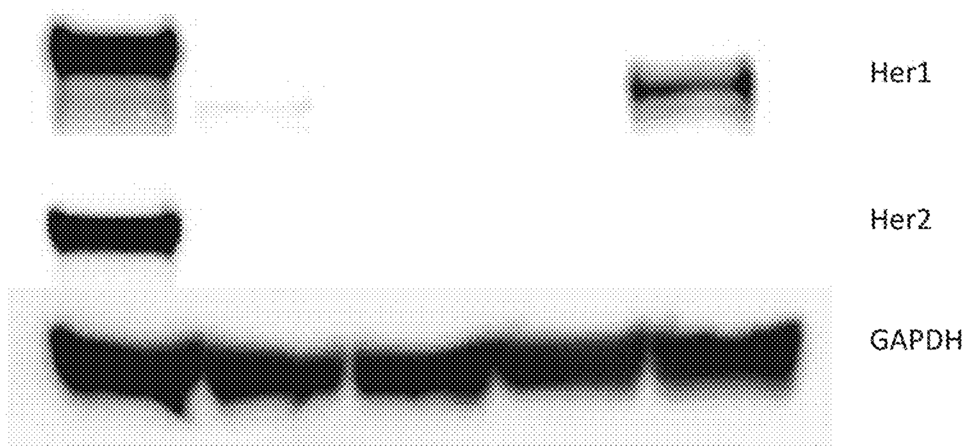
FIG. 6 depicts the immunoblot result of HER1 and HER2 double knockout clones using antibodies against HER1 and HER2 receptors. Antibody against GAPDH was used a loading control.

As shown in FIG. 3, HEK293 cells expressed both HER1 and HER2 receptors. The same procedure was repeated to knockout HER1 receptor in this HER2 KO clone #1. To do so, CRISPR knockout constructs designed specifically for human HER1 were obtained from Santa Cruz Biotechnology. The constructs containing gRNA sequences direct the Cas9 protein to induce a site-specific double strand break in the HER1 genomic region, which results in the deletion after DNA repairing. The CRISPR constructs were transiently transfected into the clone #1 cells. The transfected cells were singly plated in 96-well plate 24 hours post-transfection. 100 single cell clones were screened by genomic PCR using the primers flanking the targeted area. Only 4 single cell clones, #10, #19, #27 and #53, showed homozygous knockout of HER1 in the genome. The deletion of HER1 receptor was confirmed by the immunoblot assay. In FIG. 6, no HER1 receptor was detected in clone #10, #19 and #23. However, clone #53 showed a truncated form of HER1 receptor. Cellular lysates from these clones were also used to check the expression of HER2 receptor. All of them showed no expression of HER2 receptor. Clone #10, #19 and #27 represented homozygous knockout of both HER1 and HER2. Double knockout clone #27 (HEK293 DKO#27) was used in the following examples to generate the reporter cell to measure the activity of HER2 receptor.

Example 5

Figure 7:
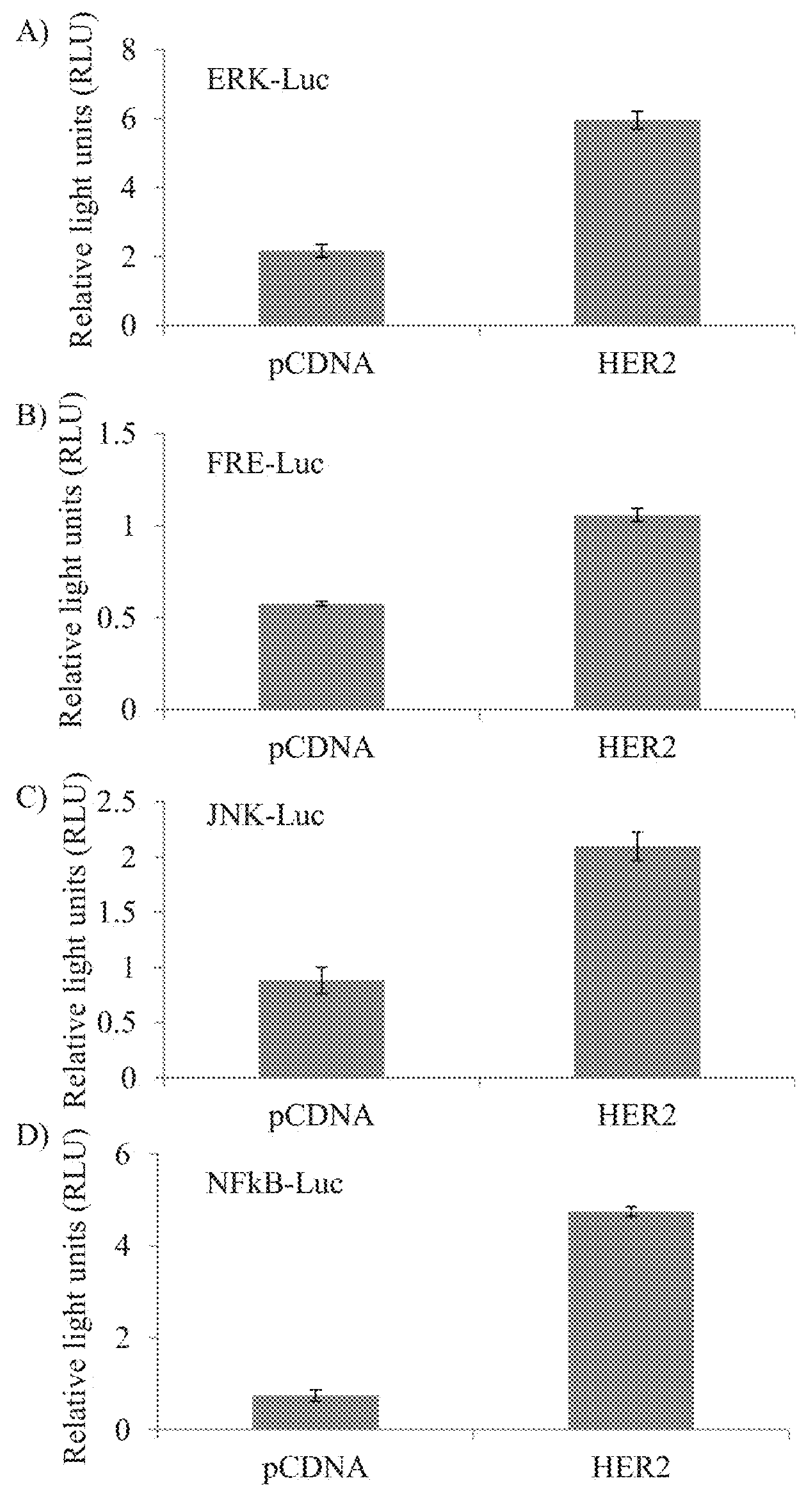
FIG. 7 depicts the luciferase reporter activity of HEK 293 cells transiently transfected with A) ERK-Luc, B) FRK-Luc, C) JNK-Luc and D) NFkB-Luc in the presence or absence of HER2 expression plasmid.

Identification of Reporters to Measure Activity of HER2 by Overexpression of HER2 Receptor Overexpression of HER2 Receptor In order to identify a reporter to measure the activity of HER2 receptor, the HEK293 cells were transfected with different reporter constructs, including ERK-Luc, FRE-Luc, JNK-Luc and NFkB-Luc, in the absence or presence of HER2 expression plasmid. After 24 hours, the luciferase reporter activity of the transfected cells was measured by Nano-Glo® Luciferase Assay (Promega). In all the reporters tested, increased reporter activity was found in the presence of HER2 receptor (FIG. 7). NFkB-Luc reporter showed the best signal to background ratio among the reporters tested.

Overexpression of HER2 Receptor Treated with Lapatinib

Figure 8:
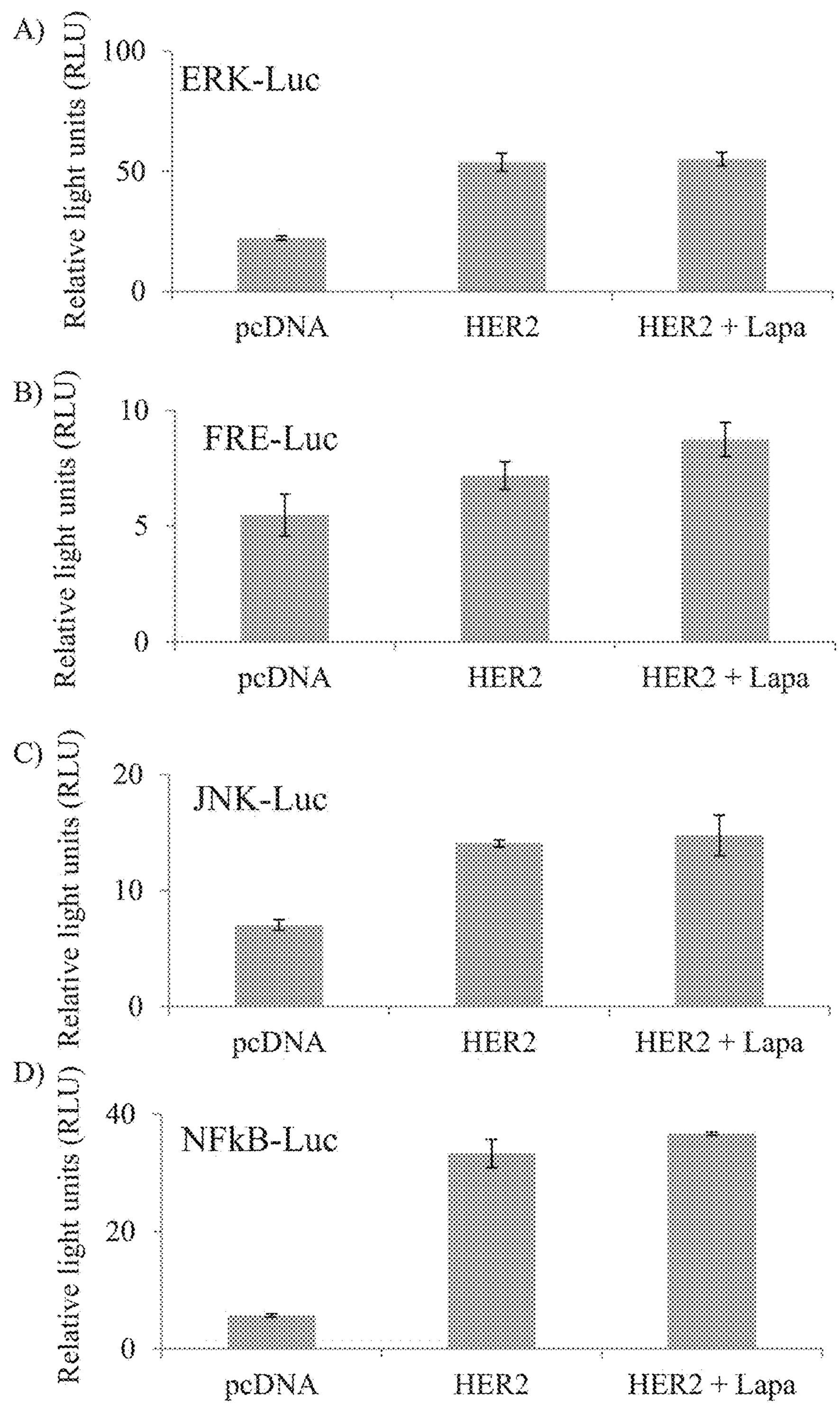
FIG. 8 depicts the luciferase reporter activity of HEK 293 cells transiently transfected with A) ERK-Luc, B) FRK-Luc, C) JNK-Luc and D) NFkB-Luc in the presence or absence of HER2 expression plasmid. The HER2 transfected cells were also treated with 10 nM of Lapatinib for 4 hours.

In order to characterize the specificity of activation of these reporters upon HER2 expression, the same transfection experiment was performed as described in Example 5a. After 24 hours, the transfected cells were treated with 10 nM of lapatinib, a tyrosine kinase inhibitor of HER2, for 4 hours. The luciferase reporter activity of the transfected cells was measured by Nano-Glo® Luciferase Assay (Promega). In all the reporters tested, increased reporter activity was found in the presence of HER2 receptor (FIG. 8). However, lapatinib did not inhibit these increased reporter activities. This observation shows that the increased reporter activities upon HER2 expression are independent of tyrosine kinase activity of HER2 receptor.

Figure 9:
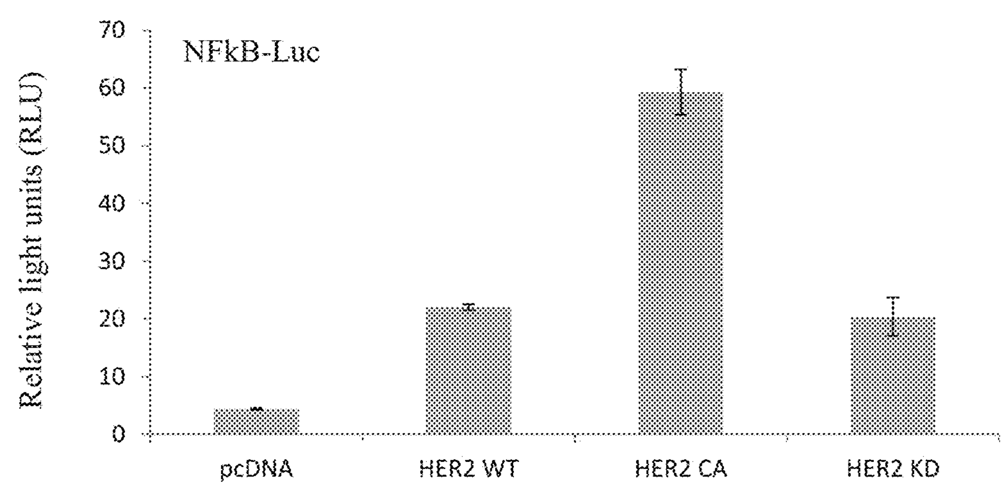
FIG. 9 depicts the luciferase reporter activity of HEK 293 cells transiently transfected with NFkB-Luc reporter in the absence or presence of wild-type (WT), constitutively active (CA) or kinase-dead (KD) of HER2 expression plasmid.

Overexpression of Wild-Type, Constitutively Active and Kinase-Dead Forms of HER2 Receptor In order to characterize the specificity of activation of NFkB-Luc reporter upon HER2 expression, a similar experiment was performed by transfecting the HER2 expression plasmids encoding wild-type, constitutively active or kinase-dead forms of HER2. After 24 hours, the luciferase reporter activity of the transfected cells was measured by Nano-Glo® Luciferase Assay (Promega). In all forms of HER2 tested, increased reporter activity was found (FIG. 9). The reporter activity was similar when the cells were transfected with either wild-type or kinase-dead form of HER2. This observation shows that the increased reporter activities upon wild-type HER2 expression are independent of tyrosine kinase activity of HER2 receptor.

Figure 10:
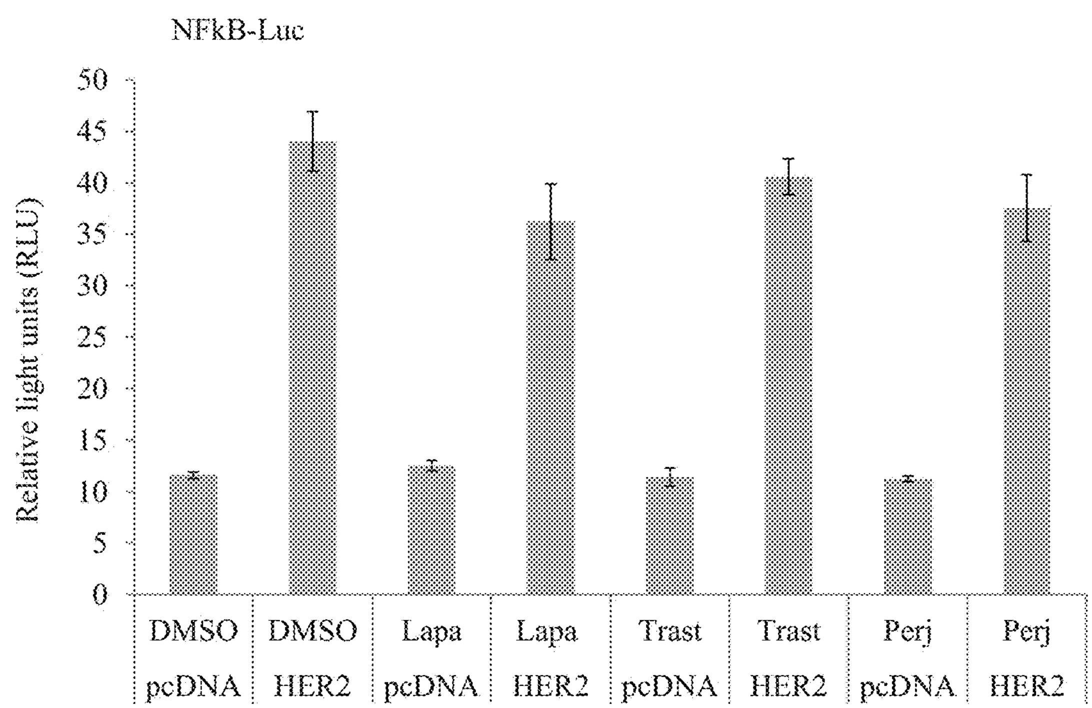
FIG. 10 depicts the luciferase reporter activity of HEK 293 cells transiently transfected with NFkB-Luc reporter in the absence or presence of HER2 expression plasmid. The transfected cells were also treated with the HER2 inhibitors including Lapatinib, Trastuzumab and Pertuzumab.

Overexpression of Wild-Type HER2 Receptor with Lapatinib, Trastuzumab and Pertuzumab In order to further characterize the specificity of activation of NFkB-Luc reporter upon HER2 expression, the HEK293 cells were transfected with the wild-type HER2 expression plasmid followed by treatment of HER2 inhibitors for 4 hours. The luciferase reporter activity of the transfected cells was measured by Nano-Glo® Luciferase Assay (Promega). Overexpression of HER2 receptor activated the NFkB-Luc reporter but none of the HER2 inhibitors block this activation (FIG. 10). This observation indicated that HER2 expression per se is not a desirableoption to measure its receptor activity and its response toward the inhibitors.

Example 6

Figure 11:
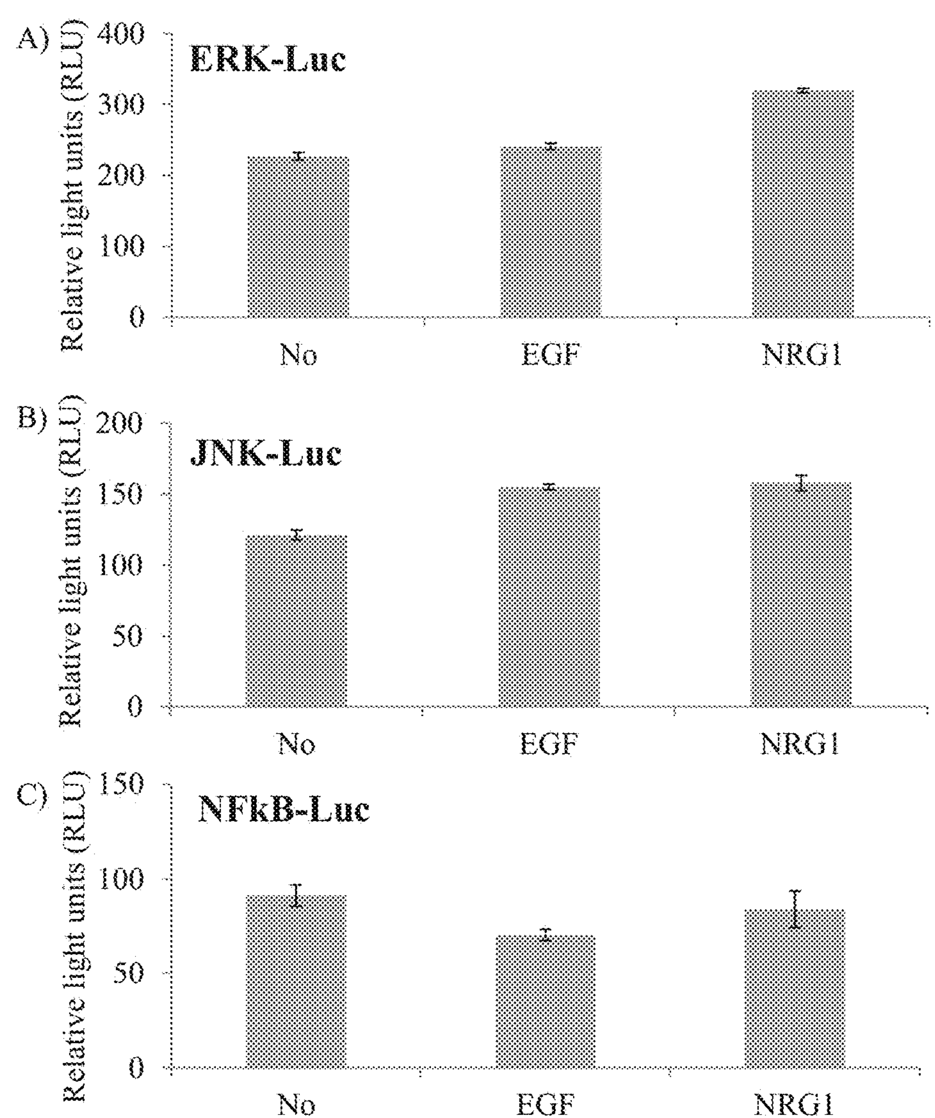
FIG. 11 depicts the luciferase reporter activity of HEK 293 cells transiently transfected with A) ERK-Luc, B) JNK-Luc, C) NFkB-Luc in the presence of HER1, HER2 and HER3 expression plasmids. The transfected cells were treated with HER1 ligand (EGF) or HER3 ligand (NRG-1).

Identification of Reporters to Measure Activity of HER2 by Overexpression of HER1, HER2 and HER3 Receptors Overexpression of HER1, HER2 and HER3 Receptors In order to identify reporters to measure the activity of HER2 receptor, expression plasmids of HER1, HER2 and HER3 were co-transfected with different reporter constructs, including ERK-Luc, JNK-Luc and NFkB-Luc, into the HEK293 cells. After 24 hours, the transfected cells were treated with either EGF (HER1 receptor ligand) or NRG1 (HER3 receptor ligand) for 6 hours. The luciferase reporter activity of the transfected cells was measured by Nano-Glo® Luciferase Assay (Promega). Interestingly, ERK-Luc reporter was activated upon the treatment of HER3 ligand (FIG. 11A). JNK-Luc reporter was activated when the transfected cells were treated with either HER1 or HER3 ligand (FIG. 11B). However, NFkB-Luc reporter showed no activation upon addition of either HER1 or HER3 ligand (FIG. 11C). This observation shows that either ERK-Luc or JNK-Luc can be used to measure activity of HER2 receptor.

Overexpression of HER1 and Wild-Type or Kinase-Dead HER2 Receptors

Figure 12:
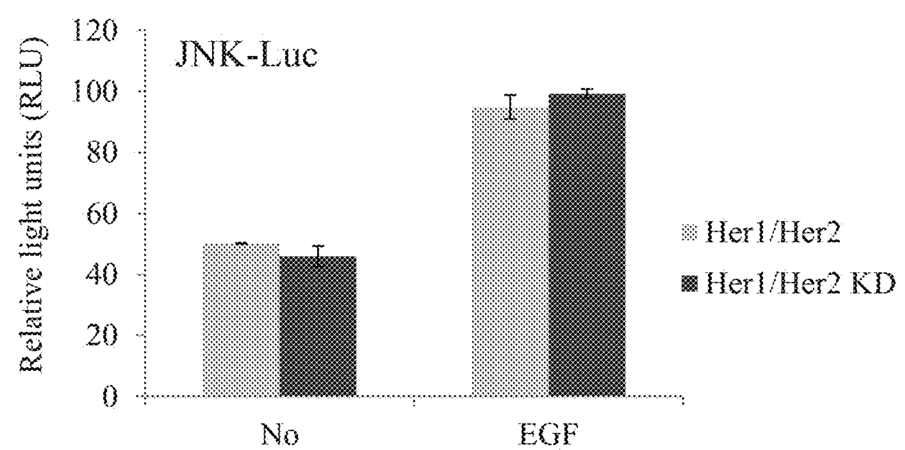
FIG. 12 depicts the luciferase reporter activity of HEK 293 cells transiently transfected with JNK-Luc reporter in the presence of HER1 and wild-type (WT) or kinase-dead (KD) HER2 expression plasmids. The transfected cells were treated with HER1 ligand (EGF).

In order to characterize the specificity of activation of JNK-Luc reporter upon treatment of HER1 ligand, JNK-Luc was co-transfected with expression plasmids of HER1 and wild-type or kinase-dead HER2 receptors into the HEK293 cells. After 24 hours, the transfected cells were treated with EGF (HER1 receptor ligand). The luciferase reporter activity of the transfected cells was measured by Nano-Glo® Luciferase Assay (Promega). In FIG. 12, no difference was found between the cells transfected with wild-type HER2 and kinase-dead HER2. In both case, the EGF treatment effectively activated the JNK-Luc reporter. This observation indicated that such activation was independent of HER2's kinase activity.

Overexpression of HER3 and Wild-Type or Kinase-Dead HER2 Receptors

Figure 13:
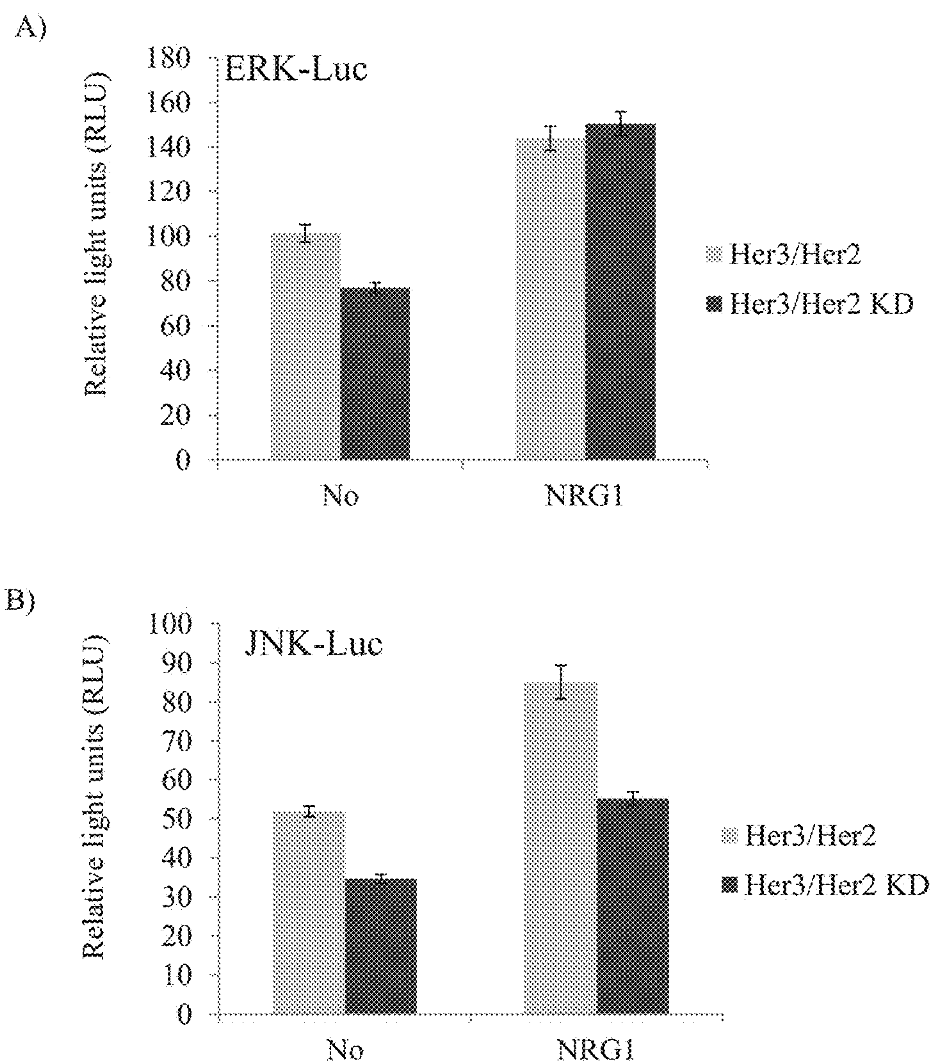
FIG. 13 depicts the luciferase reporter activity of HEK 293 cells transiently transfected with A) ERK-Luc and B) JNK-Luc reporters in the presence of HER3 and wild-type (WT) or kinase-dead (KD) HER2 expression plasmids. The transfected cells were treated with HER3 ligand (NRG-1).

In order to characterize the specificity of activation of ERK-Luc and JNK-Luc reporters upon treatment of HER3 ligand, ERK-Luc or JNK-Luc was co-transfected with expression plasmids of HER3 and wild-type or kinase-dead HER2 receptors into the HEK293 cells. After 24 hours, the transfected cells were treated with NRG1 (HER3 receptor ligand). The luciferase reporter activity of the transfected cells was measured by Nano-Glo® Luciferase Assay (Promega). In FIG. 13A, no difference in ERK-Luc reporter activity was found between the cells transfected with wild-type HER2 and kinase-dead HER2 after the treatment of NRG1. In both case, the NRG1 treatment effectively activated the ERK-Luc reporter. This observation indicated that such ERK-Luc activation was independent of HER2's kinase activity. However, the activity of JNK-Luc reporter was reduced in the cells transfected with kinase-dead HER2 compared to the cells transfected with wild-type HER2 (FIG. 13B). This observation indicated that overexpression of HER2 and HER3 receptors responded to NRG1 treatment, which activated JNK-Luc reporter in a HER2's kinase dependent manner.

Overexpression of HER3 and HER2 Receptors—NRG1 Dose

Figure 14:
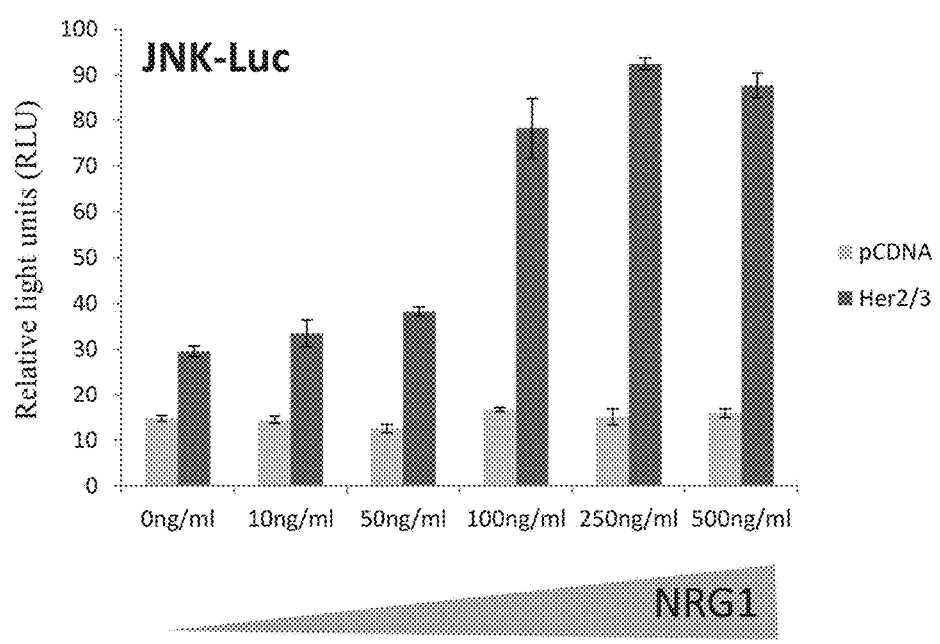
FIG. 14 depicts the luciferase reporter activity of HEK 293 cells transiently transfected with JNK-Luc reporter in the absence or presence of HER2 and HER3 expression plasmids. The transfected cells were treated with a serial dilution of HER3 ligand (NRG-1).

In order to examine the dose response of NRG1 in the activation of JNK-Luc reporters, JNK-Luc with expression plasmids of HER3 and wild-type HER2 receptors were co-transfected into the HEK293 cells. After 24 hours, the transfected cells were treated with a serial dilution of NRG1 (HER3 receptor ligand) for 6 hours. The luciferase reporter activity of the transfected cells was measured by Nano-Glo® Luciferase Assay (Promega). In FIG. 14, a dose dependent activation of JNK-Luc was shown when the cells expressed HER2 and HER3 receptors.

Modification of JNK-Luc Reporter

Figure 15:
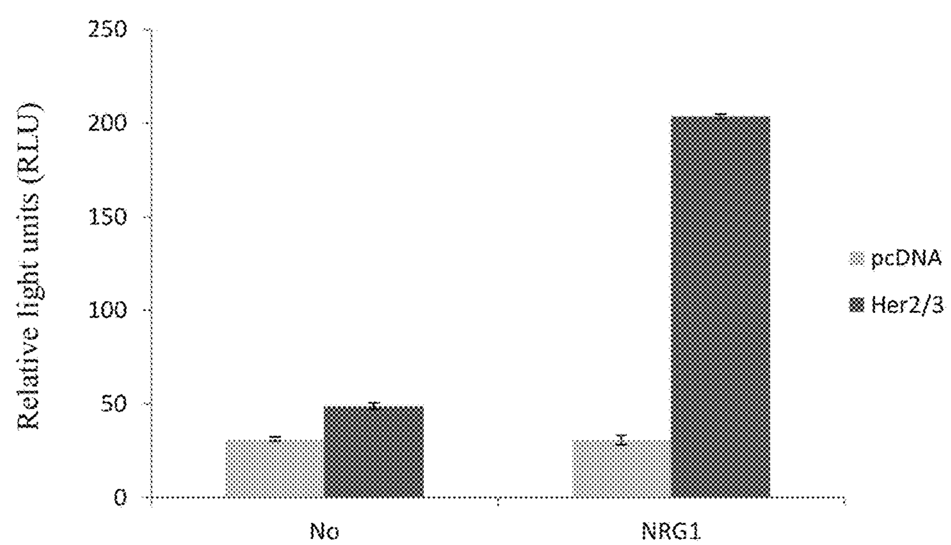
FIG. 15 depicts the luciferase reporter activity of HEK 293 cells transiently transfected with 6×JNK-Luc reporter in the absence or presence of HER2 and HER3 expression plasmids. The transfected cells were treated with HER3 ligand (NRG-1).

In the previous example, the JNK-Luc reporter contained 3 copies of AP-1 binding site. We observed around 2.6 fold induction of reporter activity when the transfected cells were treated with 100 ng/ml of NRG1 (FIG. 14). In order to enhance the activation of reporter activity, the AP-1 binding site was increased from 3 copies to 6 copies. 6×JNK-Luc was co-transfected with expression plasmids of HER3 and wild-type HER2 receptors into the HEK293 cells. After 24 hours, the transfected cells were treated with 100 ng/ml of NRG1 (HER3 receptor ligand) for 6 hours. The luciferase reporter activity of the transfected cells was measured by Nano-Glo® Luciferase Assay (Promega). In FIG. 15, the 6×JNK-Luc reporter was activated by the treatment of NRG1 only when both HER2 and HER3 receptors were expressed (FIG. 15). Approximately a 4.2 fold induction of reporter activity was found.

Example 7

Validation of Reporters to Measure Activity of HER2 by Overexpression of HER2 and HER3 Receptors in DKO#27 Cells In example 6, 6×JNK-Luc reporter was used to measure activity of HER2 in the HEK293 cells transfected with the expression constructs of HER2 and HER3. Since these cells expressed HER2 receptor, the same reporter experiment was performed using DKO#27 cells, in which both HER1 and HER2 reporters were deleted. This reporter system was also validated using inhibitors of HER2 and mutants of HER2 receptors.

6×JNK-Luc Reporter in the DKO#27 Cells—NRG1 Dose

Figure 16:
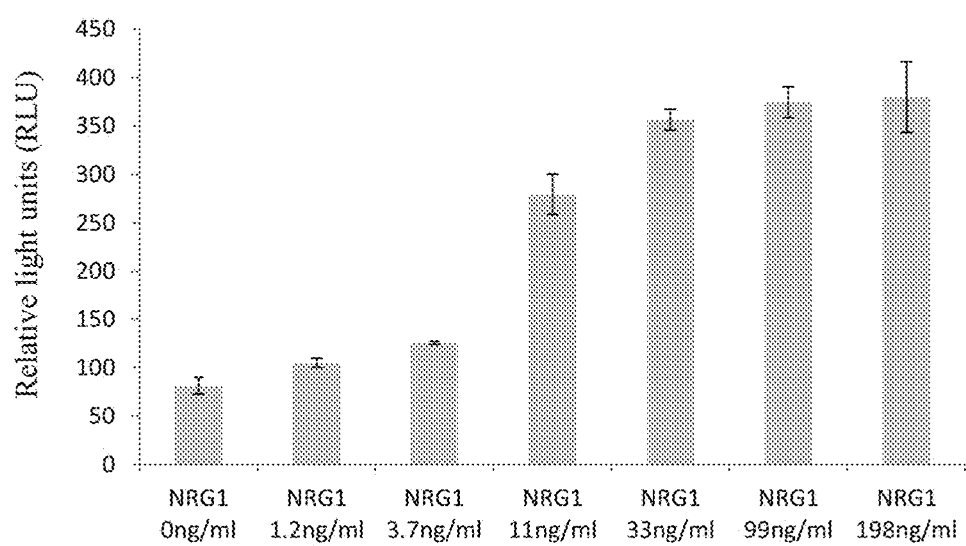
FIG. 16 depicts the luciferase reporter activity of double knockout clone #27 (HEK293 DKO#27) transiently transfected with 6×JNK-Luc reporter in presence of HER2 and HER3 expression plasmids. The transfected cells were treated with a serial dilution of HER3 ligand (NRG-1).

In example 4, the generation double knockout cells (HEK293 DKO#27) of HER1 and HER2 receptors was described. No protein expression of HER1 and HER2 receptors was detected by immunoblot assays. In order to characterize whether these cells are desirable for use in the assay of the invention, 6×JNK-Luc was co-transfected with expression plasmids of HER3 and wild-type HER2 receptors. After 24 hours, the transfected cells were treated with a serial dilution of NRG1 (HER3 receptor ligand) for 6 hours. The luciferase reporter activity of the transfected cells was measured by Nano-Glo® Luciferase Assay (Promega). In FIG. 16, a dose dependent activation of JNK-Luc was observed in these transfected cells.

6×JNK-Luc Reporter in the DKO#27 Cells—HER2 Inhibitors

HER2 inhibitors include tyrosine kinase inhibitors (Lapatinib) and monoclonal antibodies (Trastuzumab and Pertuzumab). HER2 receptor is a transmembrane receptor; it has an extracellular binding component, a transmembrane component and an intracellular tyrosine kinase component. Tyrosine kinase inhibitors bind to the tyrosine kinase domain in the HER2 and stops activation of the signaling pathway. Monoclonal antibodies bind to the extracellular component of the HER2 and stop the receptor activation. [this paragraph is already in the detailed description]

Figure 17:
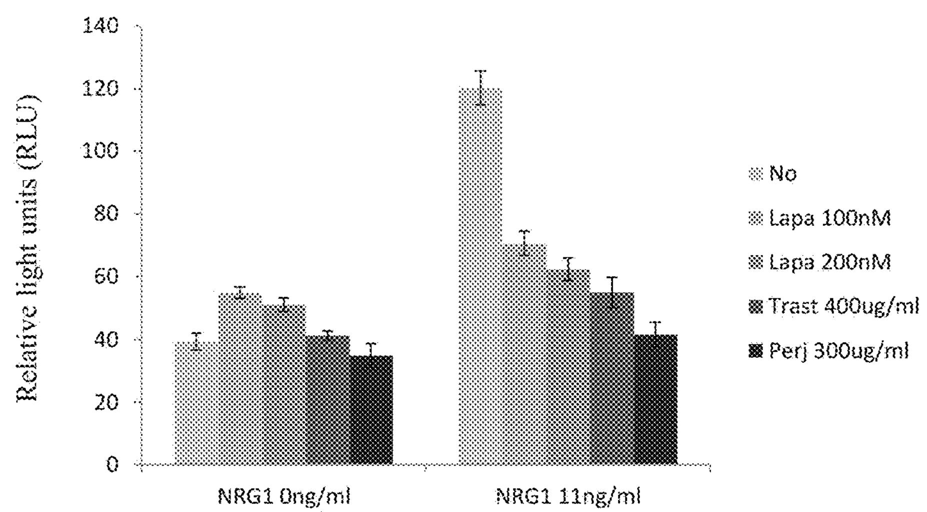
FIG. 17 depicts the luciferase reporter activity of double knockout clone #27 (HEK293 DKO#27) transiently transfected with 6×JNK-Luc reporter in presence of HER2 and HER3 expression plasmids. The transfected cells were treated with HER3 ligand (NRG-1) in the presence or absence of inhibitors of HER2.

In order to validate the requirement of HER2 receptor in the activation of 6×JNK-Luc reporter in response to NRG1 treatment, the DKO#27 cells were transfected with the wild-type HER2 and HER3 expression plasmids followed by treatment of HER2 inhibitors for 6 hours. The luciferase reporter activity of the treated cells was measured by Nano-Glo® Luciferase Assay (Promega). In the absence of inhibitors, NRG1 activated the reporter (FIG. 17). Such activation was abolished when these cells were treated with the inhibitors of HER2. This observation shows that the activation was going through HER2 receptor. The 6×JNK-Luc reporter is capable of measuring the activity of HER2 and its response to the inhibitors.

6×JNK-Luc Reporter in the DKO#27 Cells—HER2 Mutants, Including Wild-Type, Kinase-Dead and Constitutively Active Forms.

Figure 18:
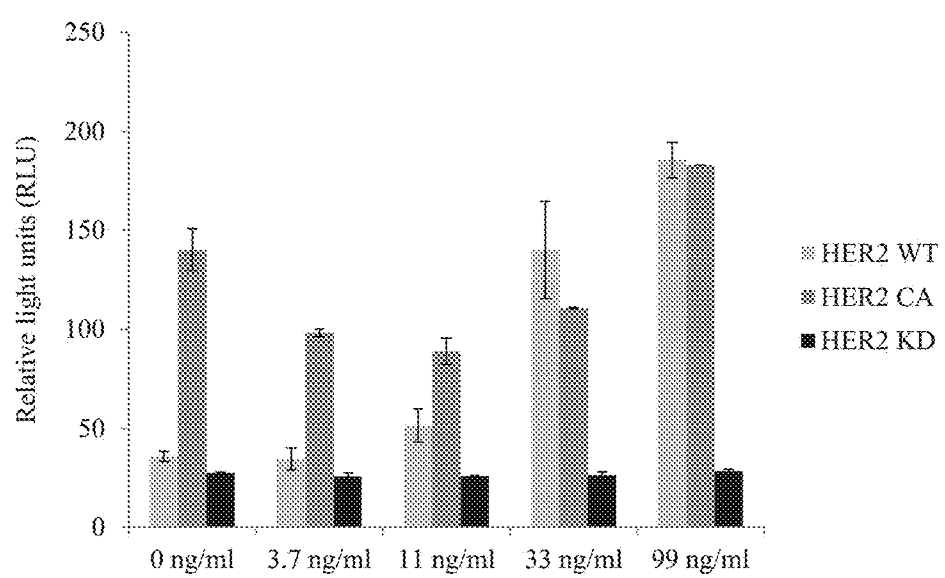
FIG. 18 depicts the luciferase reporter activity of double knockout clone #27 (HEK293 DKO#27) transiently transfected with 6×JNK-Luc reporter in presence of HER3 and wild-type (WT), constitutively active (CA) or kinase-dead (KD) HER2 expression plasmids. The transfected cells were treated with a serial dilution of HER3 ligand (NRG-1).

In order to validate that this 6×JNK-Luc reporters has the capacity of measuring HER2 receptor activity, the reporters were co-transfected with expression plasmids of HER3 and wild-type, constitutively active or kinase-dead HER2 receptors into the DKO#27 cells. After 24 hours, the transfected cells were treated with a serial dilution of NRG1. The luciferase reporter activity of the transfected cells was measured by Nano-Glo® Luciferase Assay (Promega). The transfected cells expressed wild-type form of HER2 receptor showed a dose dependent response upon the treatment of NRG1 (FIG. 18). When the cells were transfected with the constitutively active form of HER2 receptor, the reporter activity was activated without the treatment of NRG1. However, no activation of reporter was detected when the cells were transfected with kinase-dead form of HER2 receptor. These observations show that 6×JNK-Luc reporter can be used to measure the activity of HER2 receptor.

Example 8

Construction and Characterization of Stable Reporter Cells Containing 6×JNK-Luc Reporter Plasmid The 6×JNK-Luc reporter system has been validated by multiple approaches. This reporter system can be used to measure the HER2 receptor activity, its response toward the inhibitors and the mutation effect on the activity of HER2 receptor. In a preferred embodiment this reporter system is used as a clinical diagnostic test. To improve the reporter system for use in a clinical setting, reporter cells were generated in which the 6×JNK-Luc plasmid was stably integrated in the genome of DKO#27 cells.

Selection of Stable Cell Clones Carrying 6×JNK-Luc Plasmid

Since the 6×JNK-Luc plasmid did not contain a selectable marker, the 6×JNK-Luc was co-transfected with pIRES-hygB, which contained hygomycin B resistance gene, in 5:1 ratio into DKO#27 cells. Antibiotic, hygromycin B, was added to the culture medium 48 hours post-transfection. Any cells surviving through the selection process suggested that those cells not only expressed hygomycin B resistance gene, which was encoded in pIRES-hygB plasmid, but also carried the 6×JNK-Luc reporter plasmid as the co-transfection of 6×JNK-Luc with pIRES-hygB was performed in 5:1 ratio.

Characterization of Single Cell Clones after Hygomycin B Selection

Figure 19:
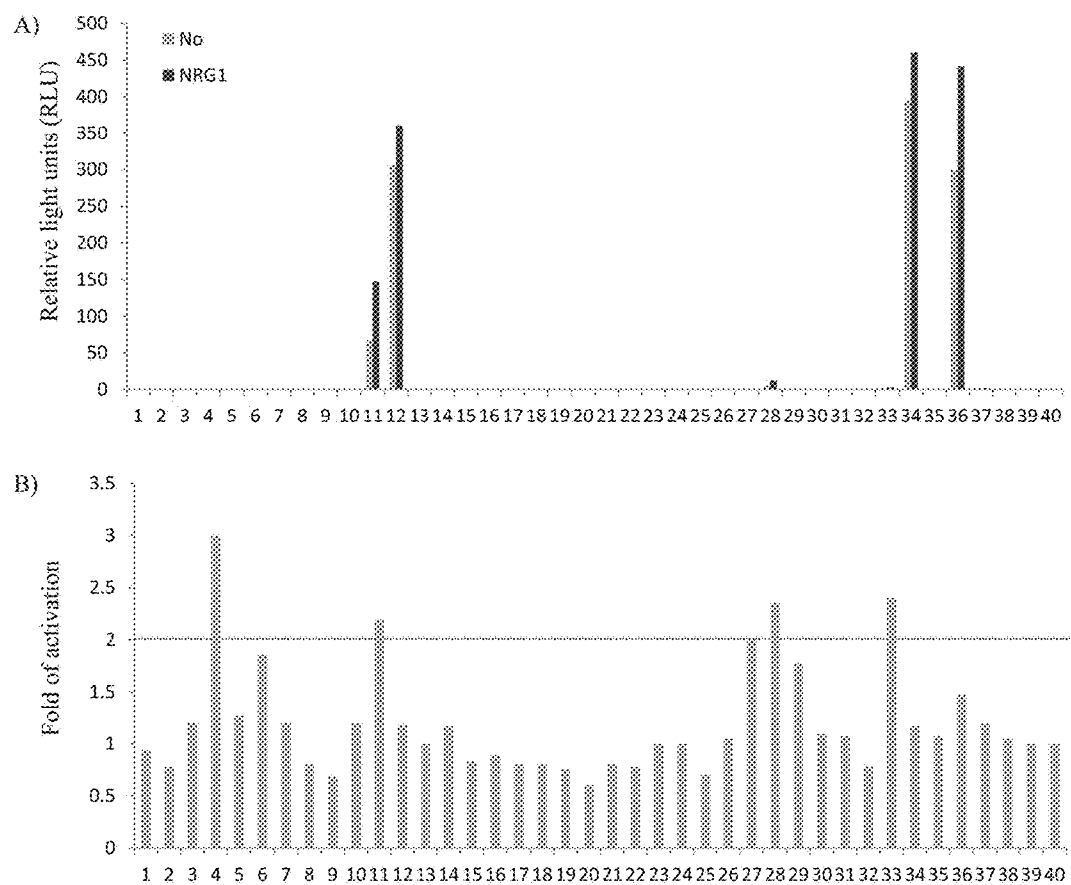
FIG. 19 depicts the luciferase reporter activity of single cell clones stably integrated with 6×JNK-Luc. These single cell clones were transiently transfected with HER2 and HER3 expression plasmids followed by treatment of NRG1. A) Relative luciferase activity was shown. B) Fold of activation upon the treatment of NRG1 was calculated.

Forty single cell clones were selected from the selection plate and were expanded. In order to confirm the integration of the 6×JNK-Luc reporter plasmid, these single cell clones were transfected with the expression plasmids of HER2 and HER3 receptors. After 24 hours, the transfected cells were stimulated with NRG1 for 6 hours. The luciferase reporter activity was measured by Nano-Glo® Luciferase assay (Promega) (FIG. 19A). Four out of forty clones showed detectable basal luciferase reporter activity in the absence of NRG1. Upon treatment with the NRG1, seven out of forty clones showed activation of the luciferase reporter activity (FIG. 19B). Among these 7 clones, clone #4, #11, #28 and #33 showed the best fold of induction (>2 folds). Therefore, these four clones were used for further analysis.

Comparison of Reporter Activity in the Clone #4, #11, #28 and #33 Upon the Treatment of NRG1

Figure 20:
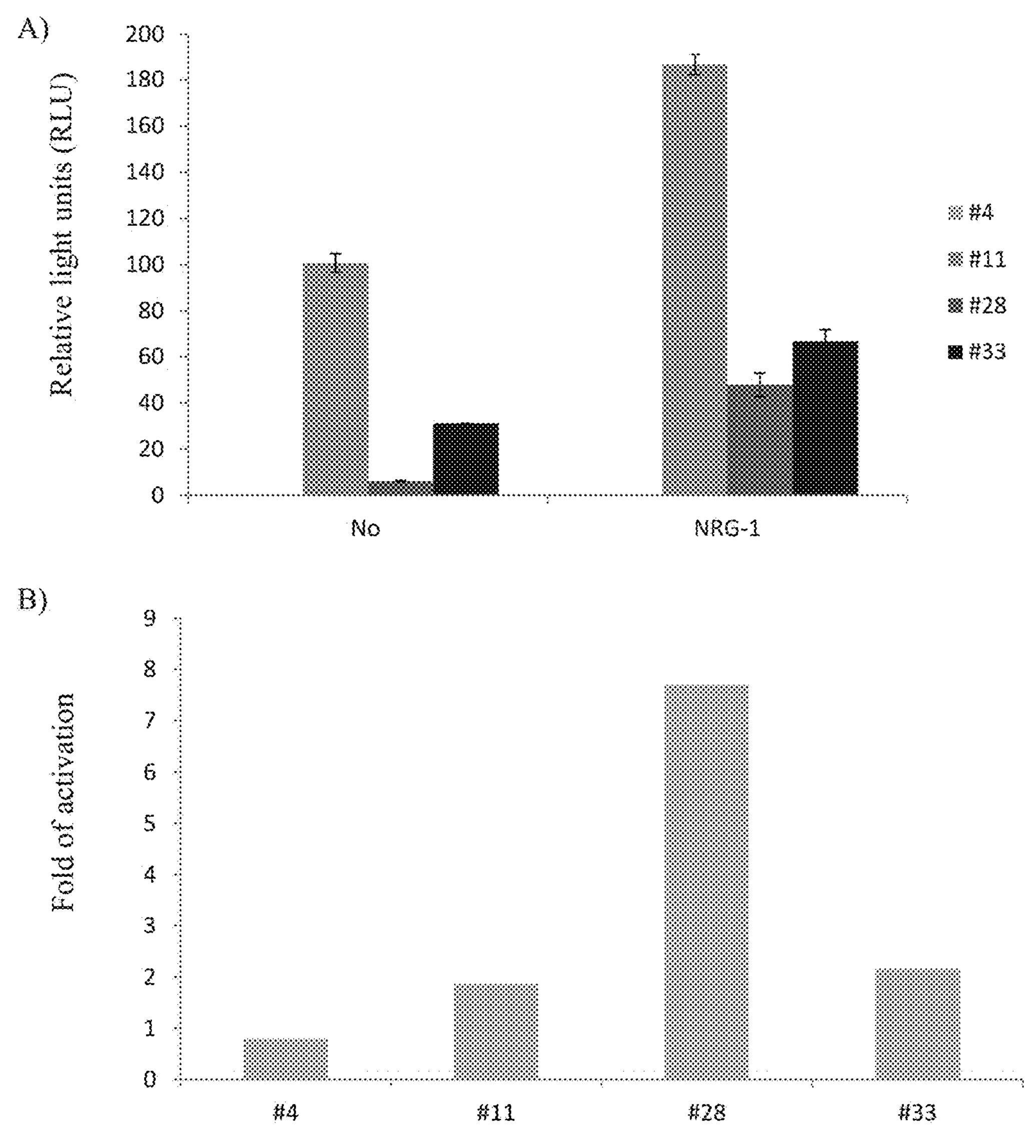
FIG. 20 depicts the luciferase reporter activity of single cell clones #4, 11, 28 and 33, which were stably integrated with 6×JNK-Luc. These single cell clones were transiently transfected with HER2 and HER3 expression plasmids followed by treatment of NRG1. A) Relative luciferase activity was shown. B) Fold of activation upon the treatment of NRG1 was calculated.

The 6×JNK-Luc single cell clones #4, #11, #28 and #33were transfected with the expression plasmids of HER2 and HER3 receptors. After 24 hours, the transfected cells were stimulated with the NRG1 for 6 hours. The luciferase reporter activity was measured by Nano-Glo® Luciferase assay (Promega) (FIG. 20A). No reporter activity was detected in the clone #4. Clone #11 has the highest basal reporter activity among those tested. Upon the treatment of NRG1, clone #28 showed the best fold of activation of reporter among these 4 clones (FIG. 20B). Therefore, clone #28 was chosen for further characterization and validation.

Figure 21:
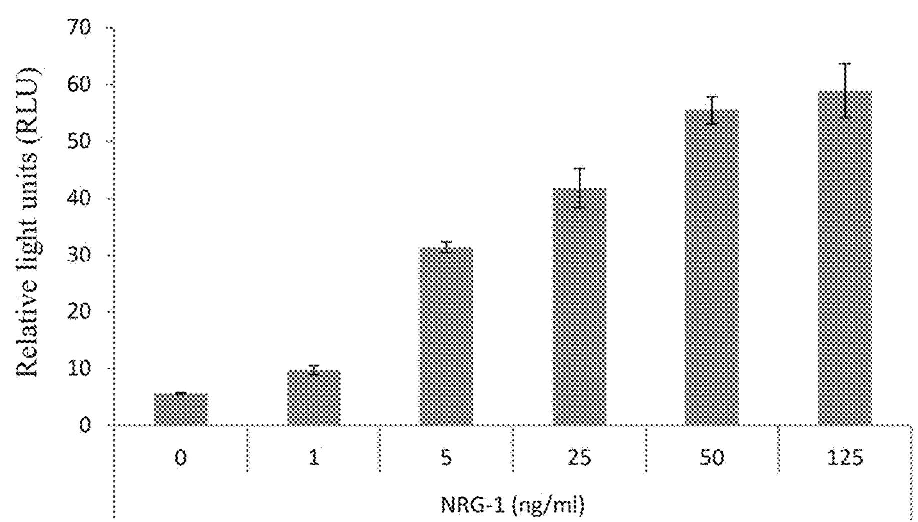
FIG. 21 depicts the luciferase reporter activity of single cell clone #28 transiently transfected with the HER3 expression plasmid and the linear expression cassette of HER2. The transfected cells were treated with a serial dilution of HER3 ligand (NRG-1).

Dose Response Curve of NRG1 Using Clone #28—HER3 Plasmid and HER2 Linear Expression Cassette In the assay of the invention, expression of patient HER2 receptor is in the linear expression cassette format instead of plasmid DNA. Therefore, the clone #28 cells were transfected with HER3 expression plasmid and HER2 linear expression DNA. After 24 hours, the transfected cells were stimulated with a serial dilution of NRG1 for 6 hours. The luciferase reporter activity was measured. This clone responded to the treatment of NRG1 in a dose dependent manner (FIG. 21). Therefore, this clone can be used to measure HER2 receptor activity by transfecting linear expression DNA of HER2.

Figure 22:
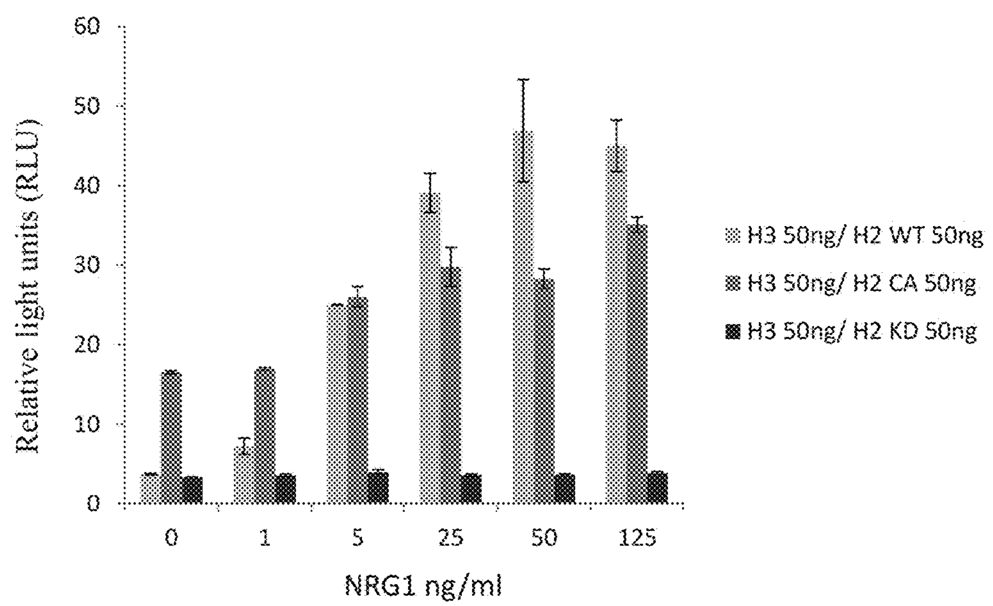
FIG. 22 depicts the luciferase reporter activity of single cell clone #28 transiently transfected with the HER3 expression plasmid and the linear expression cassette of wild-type (WT), constitutively active (CA) or kinase-dead (KD) of HER2. The transfected cells were treated with a serial dilution of HER3 ligand (NRG-1).

Dose Response Curve of NRG1 Using Clone #28—HER3 Plasmid and HER2 Linear Expression Cassette of Wild-Type, Constitutively Active or Kinase-Dead In order to validate that the clone #28 cells was capable to measure the HER2 receptor activity, expression plasmids of HER3 were co-transfected with wild-type, constitutively active or kinase-dead HER2 receptors. After 24 hours, the transfected cells were treated with a serial dilution of NRG1. The luciferase reporter activity of the transfected cells was measured by Nano-Glo® Luciferase Assay (Promega). The transfected cells expressing wild-type form of HER2 receptor showed a dose dependent response upon the treatment of NRG1 (FIG. 22). When the cells transfected with the constitutively active form of HER2 receptor, the reporter activity was activated without the treatment of NRG1. However, no activation of reporter was detected when the cells were transfected with kinase-dead form of HER2 receptor. These observations show that the clone #28 cells can be used to measure the activity of HER2 receptor.

Inhibition of Clone #28 by Inhibitors of HER2

HER2 inhibitors include tyrosine kinase inhibitors (Lapatinib) and monoclonal antibodies (Trastuzumab and Pertuzumab). HER2 receptor is transmembrane receptors; it has an extracellular binding component, a transmembrane component and an intracellular tyrosine kinase component. Tyrosine kinase inhibitors bind to the tyrosine kinase domain in the HER2 and stops activation of the signaling pathway. Monoclonal antibodies bind to the extracellular component of the HER2 and stop the receptor activation.

Figure 23:
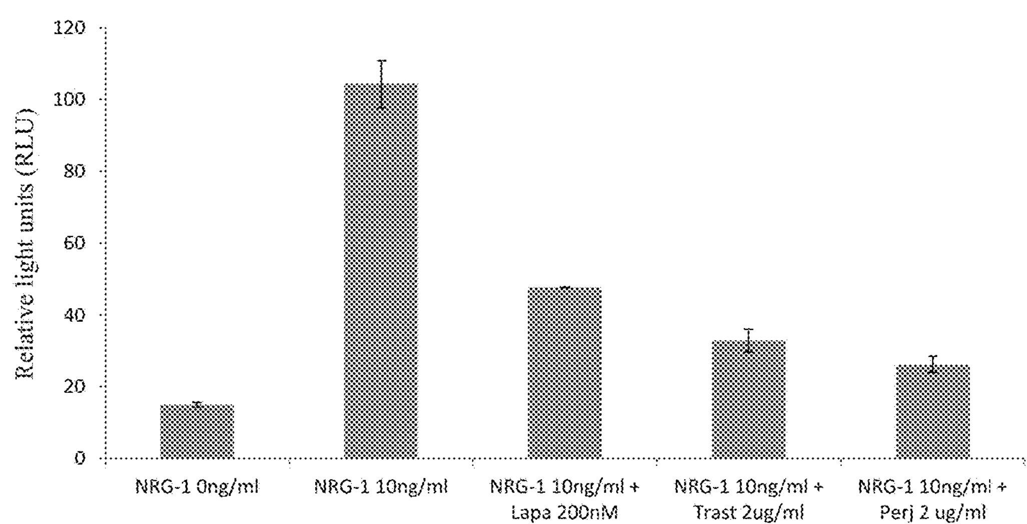
FIG. 23 depicts the luciferase reporter activity of single cell clone #28 transiently transfected with the HER3 expression plasmid and the linear expression cassette of wild-type (WT) HER2. The transfected cells were treated with NRG1 and HER2 inhibitors including Lapatinib, Trastuzumab and Pertuzumab.

In order to validate that the clone #28 reporter cells were capable of measuring the response of HER2 receptor to its inhibitors, these cells were first transfected with the HER2 linear expression DNA and HER3 expression plasmids followed by treatment of HER2 inhibitors for 6 hours in the presence of NRG1. The luciferase reporter activity of the treated cells was measured by Nano-Glo® Luciferase Assay (Promega). In the absence of inhibitors, NRG1 activated the reporter (FIG. 23). Such activation was abolished when these cells were treated with the inhibitors of HER2. This observation shows that the activation was mediated through HER2 receptor. The clone #28 cells are capable of measuring the activity of HER2 and its response to the inhibitors.

Example 9

Construction and Validation of Reporter Cells Stably Expressing HER3 Receptor Selection of Stable Cell Clones Expressing HER3 Receptor In order to simplify the invention assay, reporter cell clone #28 was modified. Selection and generation of single cell clone, which stably expressed HER3 receptor, were performed. To do so, expression construct of HER3 receptor was transfected into the reporter cell clone #28. Antibiotic, G418, was added to the culture medium 48 hours post-transfection. Any cells surviving through the selection process suggested that expression construct of HER3 was integrated into the genome.

Characterization of Single Cell Clones after G418 Selection

Figure 24:
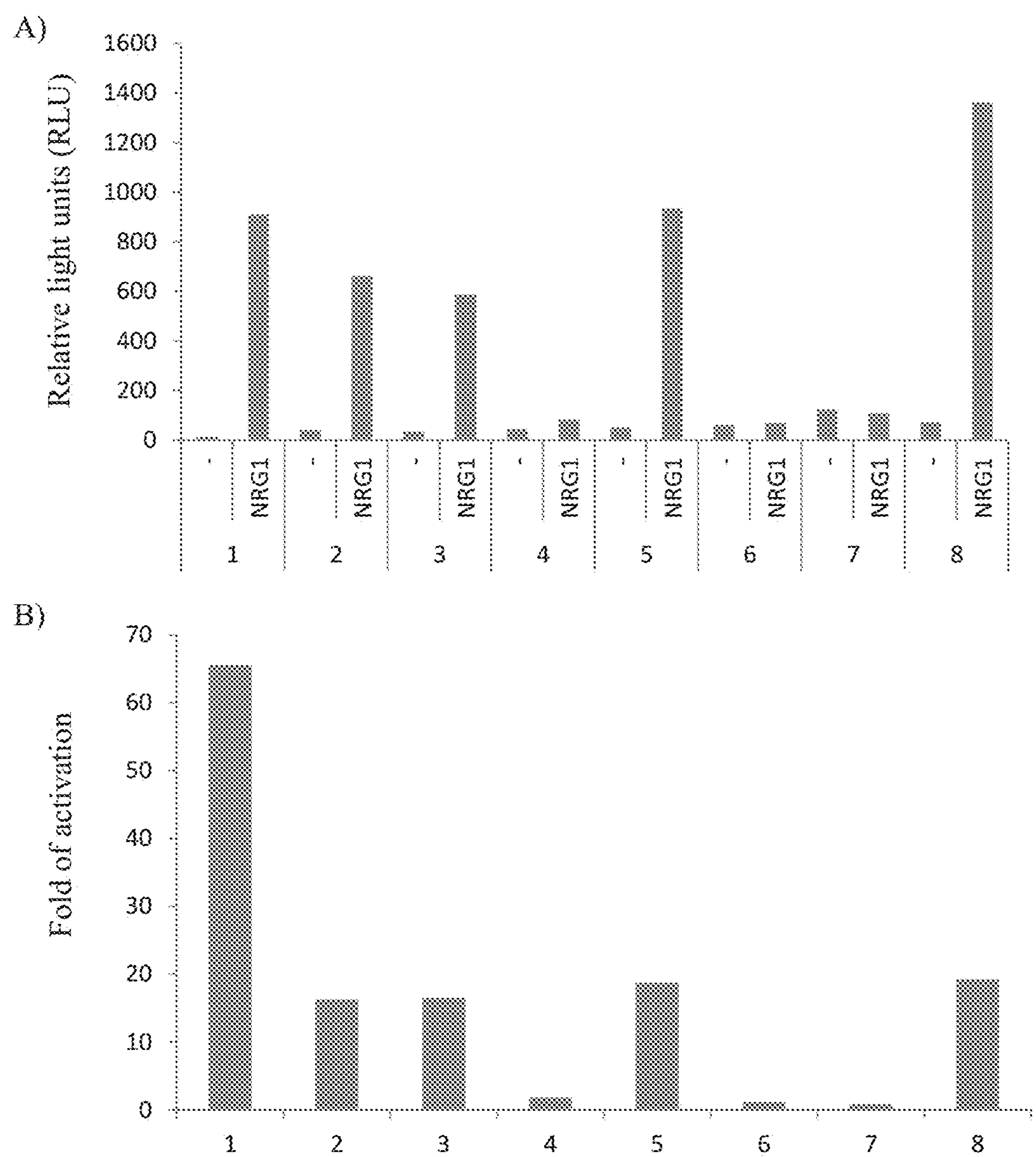
FIG. 24 depicts the luciferase reporter activity of eight single cell clones stably integrated with 6×JNK-Luc and HER3 expression plasmid. These single cell clones were transiently transfected with HER2 expression plasmid followed by treatment of NRG1. A) Relative luciferase activity was shown. B) Fold of activation upon the treatment of NRG1 was calculated.

Eight single cell clones were selected from the selection plate and were expanded. In order to confirm the expression of HER3 receptor, these single cell clones were transiently transfected with the expression plasmid of HER2. After 24 hours, the transfected cells were treated with NRG1 for 6 hours. The luciferase reporter activity was measured by Nano-Glo® Luciferase assay (Promega) (FIG. 24A). Five out of eight clones showed pronounced luciferase reporter activity upon addition of NRG1. Among these 5 clones, clone #1 showed the best fold of induction (FIG. 24B). Therefore, this clone was used for further analysis.

Figure 25:
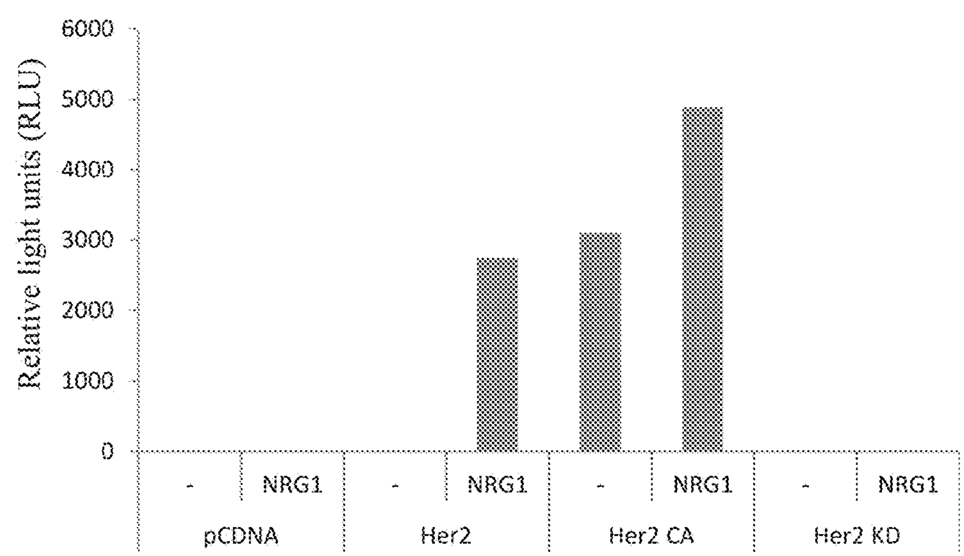
FIG. 25 depicts the luciferase reporter activity of the HER2 reporter cell transiently transfected with the wild-type (WT), constitutively active (CA) or kinase-dead (KD) of HER2 expression plasmid in the 384-well plate. The transfected cells were treated with HER3 ligand (NRG-1).

The HER2 Reporter Cells (Clone #1) to Measure Activities of WT, CA and KD of HER2 Receptor in the 384-Well Plate Clone #1 is alternately referred to as the "HER2 reporter cells". These cells were transiently transfected with the wild-type, constitutively active or kinase-dead forms of HER2 receptors in the 384-well format. After 24 hours, the transfected cells were treated with NRG1. The luciferase reporter activity of the transfected cells was measured by Nano-Glo® Luciferase Assay (Promega). The cells with no expression of HER2 receptor did not show reporter activity and did not respond to NRG1 (FIG. 25). The reporter activity of the transfected cells expressing the wild-type form of HER2 receptor was activated upon treatment with NRG1 (FIG. 25). When the cells were transfected with the constitutively active form of HER2 receptor, the reporter activity was activated in the absence of NRG1. However, no activation of reporter was detected when the cells were transfected with the kinase-dead form of HER2 receptor. These observations show that the HER2 reporter cells can be used to measure the activity of HER2 receptor.

Figure 26:
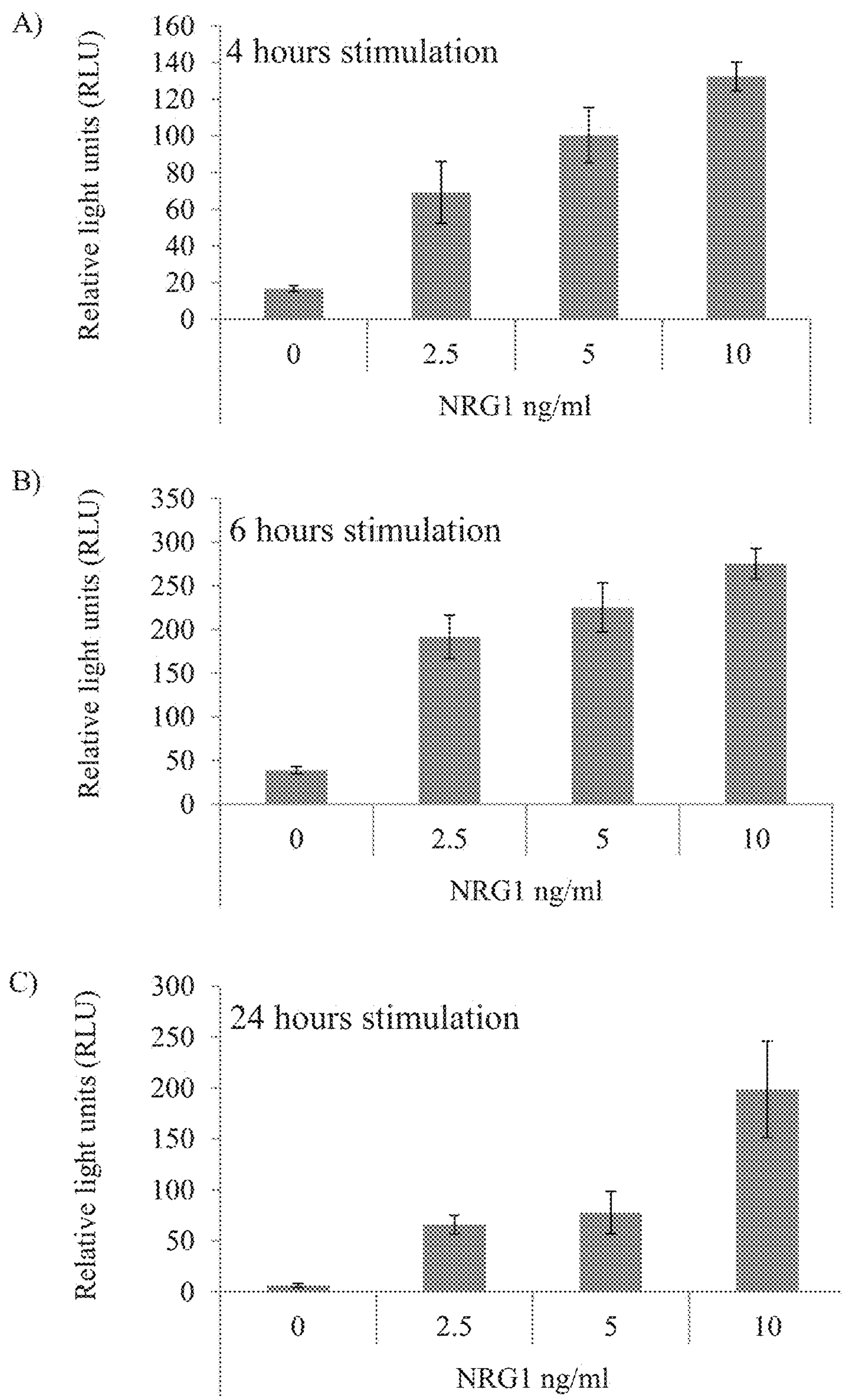
FIG. 26 depicts the luciferase reporter activity of the HER2 reporter cell transiently transfected with the linear expression cassette of HER2 in the 384-well plate. The transfected cells were treated with a serial dilution of HER3 ligand (NRG-1) for A) 4 hours, B) 6 hours and C) 24 hours.

HER2 Reporter Cells—Transiently Transfected with Linear Expression Cassette of HER2 Receptor in the 384-Well Plate The HER2 reporter cells were first transfected with 100 ng of linear expression cassette of HER2. NRG1 was added to the cells 24 hours post-transfection. Reporter assay was performed 4, 6 and 24 hours after the treatment of NRG1 (FIG. 26). All time periods showed a dose-dependent response to the treatment of NRG1. In this experiment, a better response was found when the cells were treated with NRG1 for 4 or 6 hours. A robust reporter signal was detected even at 2.5 ng/ml of NRG1.

Different Stimulation Method

Figure 27:
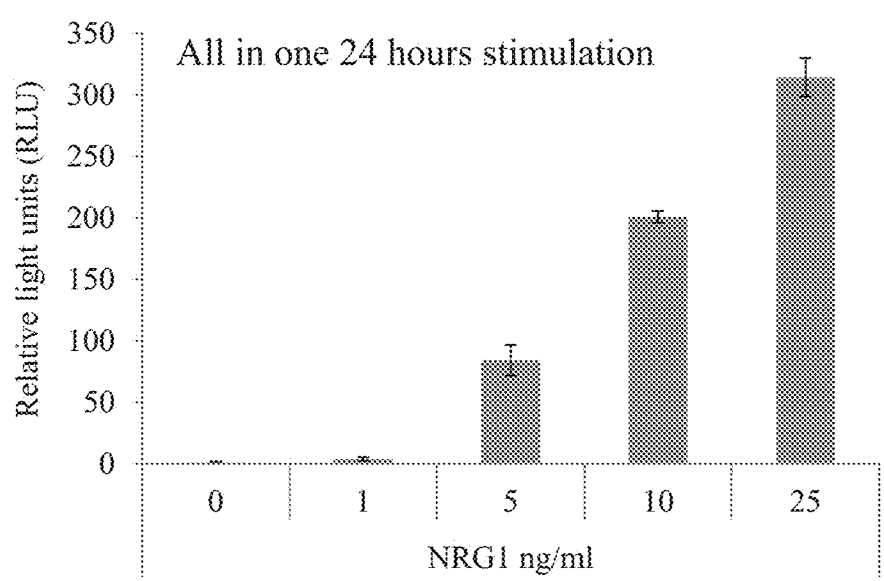
FIG. 27 A) Schematic representation of the “all-in-one” stimulation method. The NRG-1 was added to the cells together with the DNA transfection mix, i.e., at the same time. The transfected/treated cells were incubated for 24 hours. The luciferase activity was measured. B) depicts the luciferase reporter activity of the HER2 reporter cell transiently transfected with the linear expression cassette of HER2 in the 384-well plate. The transfected cells were treated with a serial dilution of HER3 ligand (NRG-1) using the “all-in-one” method.

To further reduce the assay turnaround time, different stimulation methods were explored. The first method evaluated was Example 9d which was performed by addition of NRG1 to the cells 24 hours post-transfection for 4, 6 and 24 hours. Another method was treating the cells with NRG1 when the DNA transfection complex was added to the cells. The reporter activity was measured 24 hours post-transfection (FIG. 27A). This second method is referred to herein as the "all-in-one" method. FIG. 27B shows that the all-in-one method gave a good dose response toward the treatment of NRG1. Therefore, the all-in-one method is a suitable embodiment for the HER2 assay of the invention.

Example 10

Figure 28:
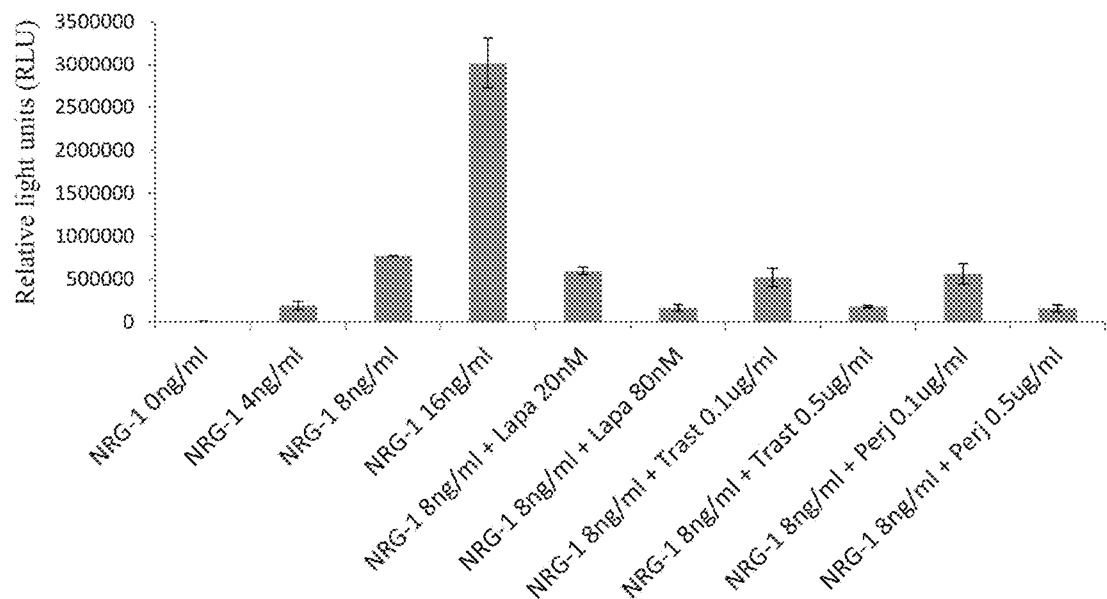
FIG. 28 depicts the receptor activity of wild-type HER2 receptor and the inhibitory activities of Lapatinib, Trastuzumab and Pertuzumab using the HER2 reporter cells transiently transfected with 50 ng of linear expression cassette of wild-type HER2. The transfected cells were treated with different concentrations of NRG-1 and HER2 inhibitors using "all-in-one" method. A) The luciferase reporter activity was measured and illustrated. B) The percentage activity of estrogen receptor was calculated and summarized in the table.

HER2 Assay Transfected with Linear Expression Cassette of Wild-Type HER2 in the 384-Well Format In example 9, the HER2 reporter cells were successfully created and the assay was validated in the 384-well format. In order to test the assay of the invention, the linear expression cassette of wild-type HER2 DNA was first transfected into the HER2 reporter cells followed by treatment with NRG1 and its inhibitors using the "all-in-one" method. The luciferase reporter activity was measured 24 hours post-transfection. Two different concentrations of inhibitors were experimentally determined and used. The low concentration of inhibitor corresponded to the concentration where treated cells retained more than 50% of HER2 activity upon NRG1 stimulation. The high concentration of inhibitor corresponded to the concentration where treated cells retained less than 50% of HER2 activity upon NRG1 stimulation. FIG. 28A shows the luciferase activity of cells transfected with linear HER2 DNA in different treatment conditions. The reporter cells responded to NRG1 stimulation in a dose dependent manner. FIG. 28B shows the calculated percentage of activity of HER2 receptor after treatment with inhibitors. These results clearly show that assay cells of the invention, in particular the HER2 reporter cells, are capable of measuring the activity of expressed HER2 receptor and its response toward the inhibitors.

Example 11

Case Studies

L755S of HER2

Figure 29:
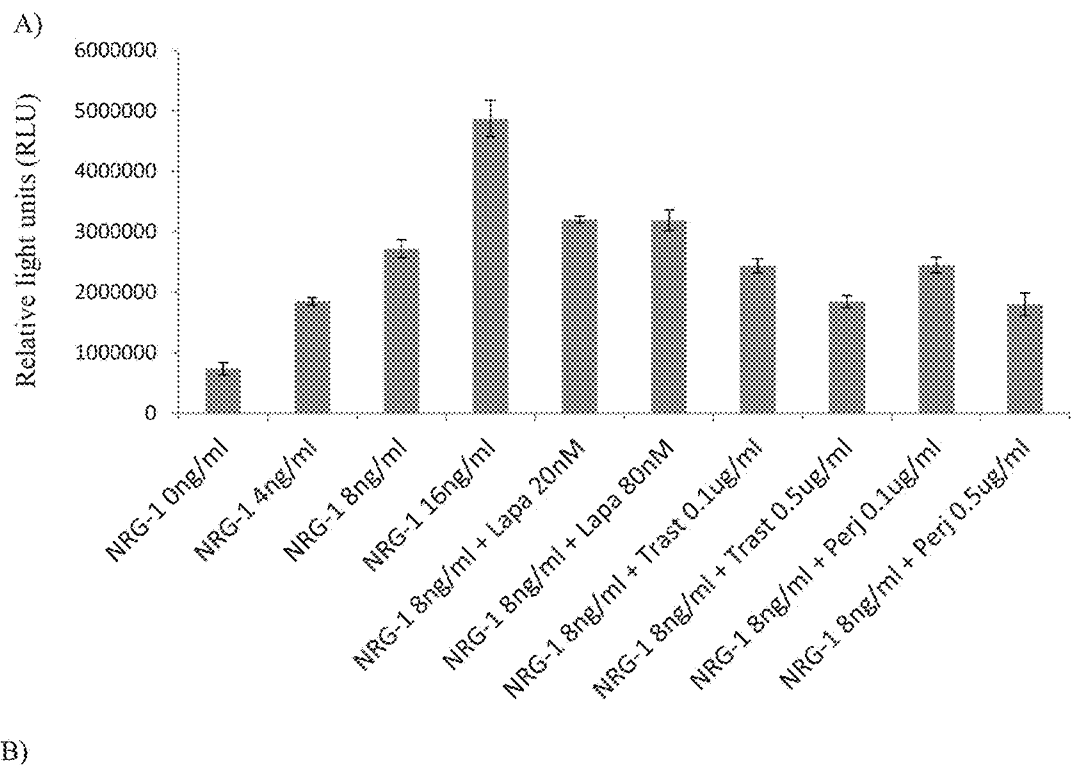
FIG. 29 depicts the receptor activity of L755S HER2 receptor and the inhibitory activities of Lapatinib, Trastuzumab and Pertuzumab using the HER2 reporter cells transiently transfected with 50 ng of linear expression cassette of L755S HER2. The transfected cells were treated with different concentrations of NRG-1 and HER2 inhibitors using the "all-in-one" method. A) The luciferase reporter activity was measured and illustrated. B) The percentage activity of estrogen receptor was calculated and summarized in the table.

L755S corresponds to a missense mutation of HER2, which changes leucine (L) into serine (S) at amino acid position of 755. In order to functionally characterize this mutation, PCR-mediated overlapping extension was employed to construct linear expression cassette of HER2 carrying this mutation. The linear expression cassette of mutant HER2 DNA was first transfected into the reporter cells followed by treatment with NRG1 and its inhibitors using the "all-in-one" method. The luciferase reporter activity was measured 24 hours post-transfection. In FIG. 29A, increased luciferase activity was observed in the reporter cells transfected with this mutant form of HER2 in the absence of NRG1. Therefore, this mutant form of HER2 is partially active and responds to treatment with NRG1.

When these cells were treated with HER2 inhibitors in the presence of NRG1, reduction of reporter activity was detected for Trastuzumab and Pertuzumab. However, the efficacy of these inhibitors was reduced. In addition, the L755S of HER2 did not respond to the lapatinib. The result is summarized in FIG. 29B. Although the mutation partially activates HER2 receptor, the L755S of HER2 still responds to the inhibitors, including Trastuzumab and Pertuzumab, with reduced efficacy. Clinically, treatment of lapatinib in this patient should be avoided because it may cause clonal expansion of cells, which carry this mutation. Therefore, Trastuzumab and Pertuzumab treatment should be recommended.

P780ins of HER2

Figure 30:
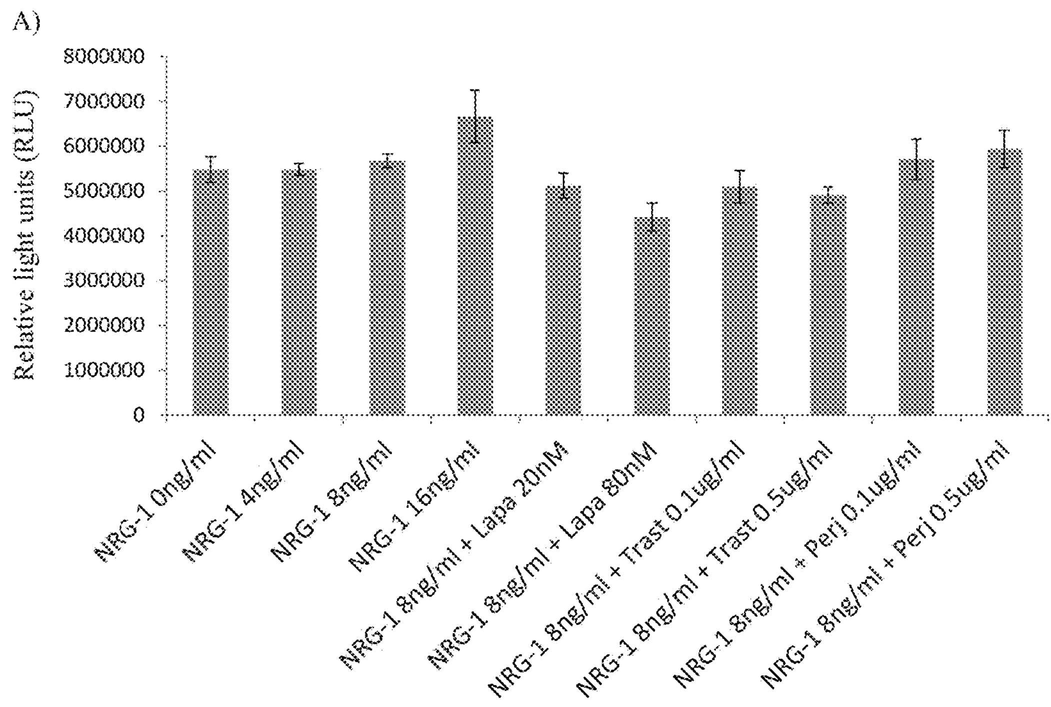
FIG. 30 depicts the receptor activity of P780ins HER2 receptor and the inhibitory activities of Lapatinib, Trastuzumab and Pertuzumab using the HER2 reporter cells transiently transfected with 50 ng of linear expression cassette of P780ins HER2. The transfected cells were treated with different concentrations of NRG-1 and HER2 inhibitors using the "all-in-one" method. A) The luciferase reporter activity was measured and illustrated. B) The percentage activity of estrogen receptor was calculated and summarized in the table.

P780ins corresponds to an insertion mutation of HER2, which adds 3 amino acids (GSP) after the amino acid position of 755 (Proline—P). In order to functionally characterize this mutation, PCR-mediated overlapping extension was employed to construct linear expression cassette of HER2 carrying this insertion. The linear expression cassette of mutant HER2 DNA was first transfected into the reporter cells followed by treatment with NRG1 and its inhibitors using the "all-in-one" method. The luciferase reporter activity was measured 24 hours post-transfection. In FIG. 30A, pronounced luciferase activity was observed in the reporter cells transfected with this mutant form of HER2 in the absence of NRG1. This mutant form of HER2 is constitutively active and its activity is independent of NRG1.

When these cells were treated with HER2 inhibitors in the presence of NRG1, very minor reduction of reporter activity was detected for lapatinib. At the high concentration of lapatinib, this mutant HER2 receptor still retained more than 75% activity compared to the cells without the treatment of inhibitor. The efficacy of this inhibitor was greatly reduced. In addition, the P780ins of HER2 did not respond to these inhibitors, including Trastuzumab and Pertuzumab. The result is summarized in FIG. 30B. Clinically, treatment of Trastuzumab and Pertuzumab in this patient should be avoided because it may cause clonal expansion of cells, which carry this mutation. Since lapatinib showed a very limited activity in the HER2 reporter assay of the invention, a higher dose of lapatinib should be used. In addition, other target therapies, such as an mTOR inhibitor or CDK4/6 inhibitor should be recommended in conjunction with the HER2 treatment (Lapatinib) to prevent potential clonal expansion of cells.

T862A of HER2

Figure 31:
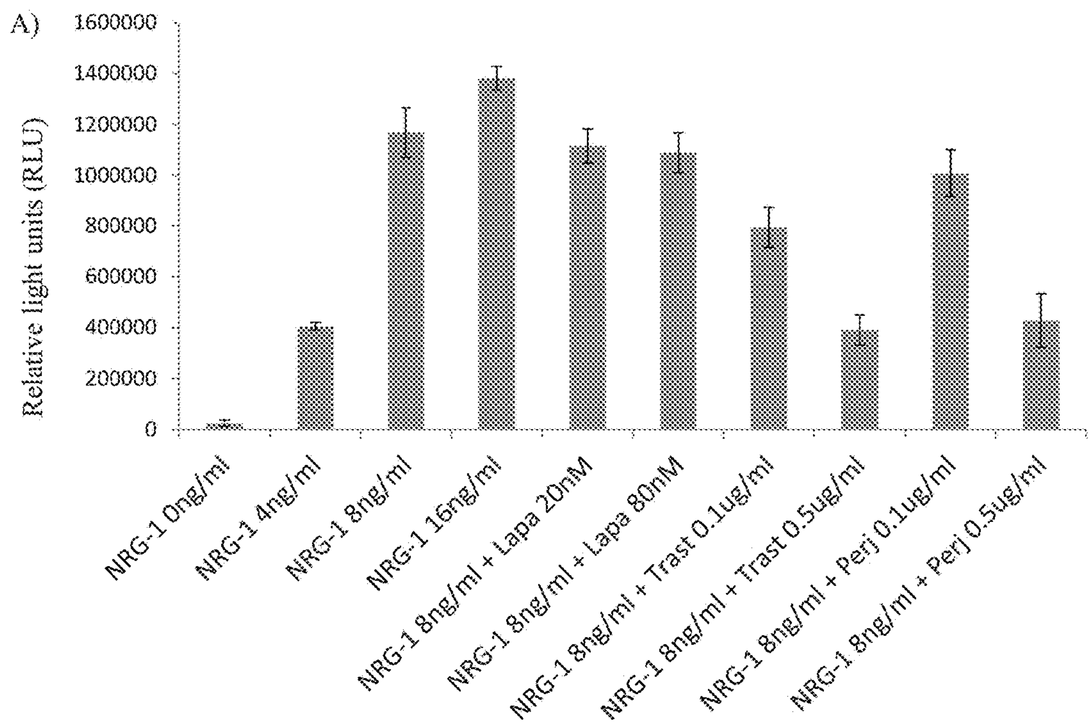
FIG. 31 depicts the receptor activity of T862A HER2 receptor and the inhibitory activities of Lapatinib, Trastuzumab and Pertuzumab using the HER2 reporter cells transiently transfected with 50 ng of linear expression cassette of T862A HER2. The transfected cells were treated with different concentrations of NRG-1 and HER2 inhibitors using the "all-in-one" method. A) The luciferase reporter activity was measured and illustrated. B) The percentage activity of estrogen receptor was calculated and summarized in the table.

T862A corresponds to a missense mutation of HER2, which changes Threonine (T) into Alanine (A) at amino acid position of 862. In order to functionally characterize this mutation, PCR-mediated overlapping extension was employed to construct a linear expression cassette of HER2 carrying this mutation. The linear expression cassette of mutant HER2 DNA was transfected into the reporter cells followed by treatment with NRG1 and its inhibitors using the "all-in-one" method. The luciferase reporter activity was measured 24 hours post-transfection. In FIG. 31A, increased luciferase activity was observed in the reporter cells transfected with this mutant form of HER2 in the presence of NRG1. Therefore, this mutant form of HER2 responds to the treatment of NRG1 in a dose-dependent manner.

When these cells were treated with HER2 inhibitors in the presence of NRG1, reduction of reporter activity was detected for Trastuzumab and Pertuzumab. However, the T862A of HER2 did not respond to the lapatinib. The result is summarized in FIG. 31B. Clinically, treatment of lapatinib in this patient should be avoided because it may cause clonal expansion of cells, which carry this mutation. Therefore, Trastuzumab and Pertuzumab treatment should be recommended.

Materials and Methods

Construction of Expression Plasmids of HER1, HER2 and HER3

Human wild-type HER1, HER2 and HER3 cDNA plasmids were ordered from Open Biosystems (GE Dharmacon). A pair of PCR primers was designed to amplify the coding region as shown below;

HHER1 NHEI F:
(SEQ ID NO: 1)
TGGCTAGCCGCCACCATGCGACCCTCCGGGACGGCC

HHER1 XHOI R:
(SEQ ID NO: 2)
GACTCGAGTCATGCTCCAATAAATTCACT

HHER2 NHEI F:
(SEQ ID NO: 3)
TGGCTAGCCGCCACCATGGAGCTGGCGGCCTTGTGC

HHER2 XHOI R:
(SEQ ID NO: 4)
GACTCGAGTCACACTGGCACGTCCAGACC

HHER3 NHEI F:
(SEQ ID NO: 5)
TGGCTAGCCGCCACCATGAGGGCGAACGACGCTCTG

HHER3 XBAI R:
(SEQ ID NO: 6)
CCTCTAGATTACGTTCTCTGGGCATTAGC

Restriction enzyme sites of NheI and XhoI were added to the forward and reverse primers respectively for the construction of HER1 and HER2 expression plasmids. Restriction enzyme sites of NheI and XbaI were added to the forward and reverse primers respectively for the construction of HER3 expression plasmid. Coding sequence of wild-type HER1, HER2 and HER3 was PCR amplified using their corresponding forward and reverse primers from cDNA plasmid using Q5® high-fidelity DNA polymerase (NEB). The amplified PCR product was run on agarose gels and purified using DNA gel purification kit from Qiagen. The gel purified PCR products and pcDNA3.1 DNA vector were treated with NheI and XhoI or XbaI restriction enzymes at 37° C. for 2 hours. The digested products were run on agarose gels and purified using DNA gel purification kit from Qiagen. The PCR fragments containing coding sequence of wild-type HER1, HER2 and HER3 were ligated with linearized pcDNA3.1 DNA vector using fast ligation kit from NEB. The ligated products were transformed into Top10 competent cell (Invitrogen). The transformed competent cells were selected using LB plate containing ampicillin for 16 hours at 37° C. The ampicillin resistant clones were cultured in 2 mL of LB medium with ampicillin for 16 hours at 37° C. DNA was extracted from the bacteria culture using DNA mini-preparation kit from Qiagene. The wild-type HER1, HER2 and HER3 expression plasmids were confirmed by both restriction enzyme digestion and DNA sequencing.

Construction of Linear Expression Cassette of Wild-Type HER2 and its Mutants

The following primers were used to construct the linear expression cassette of wild-type HER2 and its mutants:

UF-CMV F:
(SEQ ID NO: 7)
GCGTTCGCTAAGCGTAGCTAGCGATGTACGGGCCAGATA

UF:
(SEQ ID NO: 8)
GCGTTCGCTAAGCGTAGCTAG

UR-BGH R:
(SEQ ID NO: 9)
TCTGATACGTCTCGACGCACTCTCCCAGCATGCCTGCTATTG

UR:

-continued (SEQ ID NO: 10)
TCTGATACGTCTCGACGCACTC

HER2 L755S F:
(SEQ ID NO: 11)
CCAGTGGCCATCAAAGTGTCCAGGGAAAACACATCCCCC

HER2 L755S R:
(SEQ ID NO: 12)
GGGGGATGTGTTTTCCCTGGACACTTTGATGGCCACTGG

HER2 P780INS F:
(SEQ ID NO: 13)
GCTGGTGTGGGCTCCCCAGGTTCTCCCTATGTCTCCCGCCTTCTG

HER2 P780INS R:
(SEQ ID NO: 14)
CAGAAGGCGGGAGACATAGGGAGAACCTGGGGAGCCCACACCAGC

HER2 T862A F:
(SEQ ID NO: 15)
CCCAACCATGTCAAAATTGCAGACTTCGGGCTGGCTCGG

HER2 T862A R:
(SEQ ID NO: 16)
CCGAGCCAGCCCGAAGTCTGCAATTTTGACATGGTTGGG

The linear expression cassette of wild-type HER2 was amplified from the wild-type HER2 expression plasmid using UF-CMV F and UR-BGH R primers. The amplified PCR product was run on agarose gels and purified using DNA gel purification kit from Qiagen.

The linear expression cassettes of mutant forms of HER2 were prepared by PCR mediated overlapping extension. Two rounds of PCR amplification were performed. The first round of PCR included two independent PCR using UF-CMV F and mutation specific R primers or UR-BGH R and mutation specific F primers to amplify coding region of HER2 into two fragments. The PCR products were then treated with ExoSAP-IT from Affymetrix to eliminate the unincorporated primers and dNTPs. The mixture was incubated at 37° C. for 15 minutes followed by 80° C. for 15 minutes. Then, 10 ul of PCR products from each reaction were added to 30 ul of water. 5 ul of the diluted products were used as template to performed second round of PCR. In this PCR, UF and UR primers were added to the reaction to construct the linear expression cassette of HER2 carrying the desired mutation. The amplified PCR product was run on agarose gels and purified using DNA gel purification kit from Qiagen.

Construction of ERK-Luc, FRE-Luc, JNK-Luc, NFkB-Luc and 6×JNK-Luc Reporter Constructs The oligonucleotides corresponding to the binding sites of different transcriptional factors to measure the signaling activity of pathways were designed and were shown as follow:

3XERK F:
(SEQ ID NO: 17)
TCGAGGGATGTCCATATTAGGAGGATGTCCATATTAGGAGGATGTCC
ATATTAGGAA

>3XERK R:
(SEQ ID NO: 18)
AGCTTTCCTAATATGGACATCCTCCTAATATGGACATCCTCCTAATA
TGGACATCCC

>3XFRE F:

-continued (SEQ ID NO: 19)
TCGAGGATCAAGTAAACAACTATGTAAACAAGATCAAGTAAACAACT

ATGTAAACAAGATCAAGTAAACAACTATGTAAACAAA

>3XFRE R:

(SEQ ID NO: 20)
AGCTTTTGTTTACATAGTTGTTTACTTGATCTTGTTTACATAGTTGT

TTACTTGATCTTGTTTACATAGTTGTTTACTTGATCC

>3XJNK F:

(SEQ ID NO: 21)
TCGAGTGAGTCAGTGAGTCAGTGAGTCAGA

>3XJNK R:

(SEQ ID NO: 22)
AGCTTCTGACTCACTGACTCACTGACTCAC

>3XNFKB F:

(SEQ ID NO: 23)
TCGAGGGGACTTTCCGGGACTTTCCGGGACTTTCCA

>3XNFKB R:

(SEQ ID NO: 24)
AGCTTGGAAAGTCCCGGAAAGTCCCGGAAAGTCCCC

The oligonucleotides were re-suspended in TE buffer at 200 μM concentration. Equal amount of forward and reverse oligonucleotides were annealed into double strand form by incubated at 95° C. for 10 minutes. After the mixture cooled down to room temperature, 1 μl of double strand oligonucleotides was used as insert to ligate with lineralizedpNL3.2 reporter construct (Promega). The linearized vector was prepared by treating the DNA with XhoI and HindIII restriction enzymes. The ligated DNA was then transformed into Top10 competent cells (Invitrogen, Carlsbad, Calif.). These reporter constructs were confirmed by both restriction enzyme digestion and DNA sequencing.

In order to construct the 6×JNK-Luc reporter construct, oligonucleotides corresponding to three copies of AP-1 binding site were designed to measure the signaling activity of JNK pathway. The sequences were shown as follow:

3XJNK F1:

(SEQ ID NO: 25)
CTGAGTCAGTGAGTCAGTGAGTCAGC

3XJNK R1:

(SEQ ID NO: 26)
TCGAGCTGACTCACTGACTCACTGACTCAGGTAC

The oligonucleotides were re-suspended in TE buffer at 200 μM concentration. Equal amount of forward and reverse oligonucleotides were annealed into double strand form by incubated at 95° C. for 10 minutes. After the mixture cooled down to room temperature, 1 μl of double strand oligonucleotides was used as insert to ligate with lineralizedpNL3.2 reporter construct (Promega). The linearized vector was prepared by treating the DNA with KpnI and XhoI restriction enzymes. The ligated DNA was then transformed into Top10 competent cells (Invitrogen, Carlsbad, Calif.). The 6×JNK-Luc reporter construct was confirmed by both restriction enzyme digestion and DNA sequencing.

Transfection

For cell transfection experiments, HEK293 cells (ATCC) were plated at density of 4-8×104 cells per well (96-well plates) or 1-2×104 cells per well (384-well plates) in phenol red-free MEM containing 10% FBS and antibiotics. Either DNA plasmid or linear DNA was mixed with TransIT-293 transfection reagent (Mirus Bio LLC). Once cells were trypsinized, DNA transfection mix was added. The cells were then incubated for 24 or 48 hours.

Immunoblot Assay (Western Blotting)

Cells were collected 48 hours post-transfection, washed in PBS and lysed in ProteoJET mammalian cell lysis reagent (Fermentas) with protease and phosphatase inhibitors (Sigma). Lysates were centrifuged and supernatants were prepared for SDS-PAGE by addition of sample loading buffer (Bio-Rad). Lysates were subjected to 4-12% PAGE (Bio-Rad) and transferred to Immun-Blot PVDF membrane (Bio-Rad) per manufacturer's recommendations. Membranes were blocked in 5% milk/TPBT at room temperature for 1 hour. Membranes were probed with anti-HER1, anti-HER2, anti-HER3 and anti-GAPDH (Santa Cruz).

Construction and Identification of HER1 and HER2 Double Knockout Cells

In order to knockout the HER1 and HER2 receptors in the genome of HEK293 cells, the CRISPR knockout constructs designed specifically for human HER1 and HER2 were obtained from Santa Cruz Biotechnology. The constructs containing gRNA sequences direct the Cas9 protein to induce a site-specific double strand break in the HER1 and HER2 genomic region, which results in the deletion after repairing. To examine the deletion, primers were designed flanking the gRNA targeting region. These primers were used to perform genomic PCR to reveal the genomic status.

HER1 KO F1:

(SEQ ID NO: 27)
TTTCTTCCAGTTTGCCAAGG

HER1 KO R2:

(SEQ ID NO: 28)
ACGATTCCTGCTCAGCTTGT

HER2 KO F1:

(SEQ ID NO: 29)
GCAAAGGGTTTGAGTGAAGG

HER2 KO R2:

(SEQ ID NO: 30)
GCCACTATGGGAGAAAGGTG

In order to generate stable knockout HER2 cells, the HER2 CRISPR constructs were transiently transfected into the HEK293 cells. The transfected cells were singly plated in 96-well plate 24 hours post-transfection. Single cell clones were selected and expanded. Genomic DNA was prepared. PCR was performed using the primers flanking the targeted area. To further confirm the HER2 knockout status of the single cell clones, cellular extract was prepared. Immunoblot was performed using anti-Her2 antibody. Anti-GAPDH was used as a loading control.

In order to generate the double knockout cells of HER1 and HER2, the same procedure to knockout HER1 receptor was repeated in the validated HER2 KO clone. To do so, the CRISPR knockout constructs designed specifically for human HER1 were obtained from Santa Cruz Biotechnology. The constructs containing gRNA sequences direct the Cas9 protein to induce a site-specific double strand break in the HER1 genomic region, which results in the deletion after DNA repairing. The CRISPR constructs were transiently transfected into the clone #1 cells. The transfected cells were singly plated in 96-well plate 24 hours post-transfection. We screen 100 single cell clones by genomic PCR using the primers flanking the targeted area. The deletion of HER1 receptor was further confirmed by the immunoblot assay.

What is claimed is:

1. A method of determining whether an HER2 variant is sensitive to treatment with a HER2 inhibitor in a cell, comprising the steps of:

a) preparing a cDNA encoding said HER2 variant;

b) preparing an expression cassette containing the HER2 variant cDNA;

c) transfecting said prepared expression cassette containing said HER2 variant cDNA in an assay cell having a JNK reporter construct having SEQ ID NO: 31 comprising a reporter gene cDNA linked to at least one AP-1 binding site, and said cell is capable of expressing HER3, wherein the HER2 variant and HER3 are expressed;

d) exposing said transfected cell to a HER3 ligand, wherein HER3 complexes with said HER2 variant to form a dimer which thereby activates the JNK reporter construct and generates a signal;

e) exposing said transfected cell with an HER2 inhibitor; and f) determining whether said HER2 variant is sensitive to treatment with said HER2 inhibitor by measuring a change in signal.

2. The method of claim 1, wherein said HER2 variant contains a missense mutation, insertion, or deletion.

3. The method of claim 1 wherein the expression cassette containing the HER2 variant cDNA is a linear expression cassette.

4. The method of claim 1 wherein said assay cell has a double knockout of HER1 and HER2.

5. The method of claim 1 wherein the JNK reporter construct comprises a reporter gene cDNA linked to 3 to 12 AP-1 binding sites.

6. The method of claim 1 wherein the INK reporter construct comprises a reporter gene cDNA linked to 6 AP-1 binding sites.

7. The method of claim 1 wherein said assay cell further comprises a HER3 expression construct.

8. The method of claim 7 wherein said HER3 expression construct is stably integrated into the assay cell.

9. The method of claim 1 wherein said JNK reporter construct is stably integrated into the assay cell.

10. The method of claim 1, wherein step c) and step d) are performed simultaneously.

11. The method of claim 1 wherein steps a) through f) are performed in 32 hours or less.

12. The method of claim 1, wherein said HER2 inhibitor is Lapatinib, Trastuzumab, or Pertuzumab.

13. The method of claim 1, wherein said reporter gene cDNA encodes luciferase, said signal is light emission produced upon addition of a substrate for said luciferase, and a decrease in light emission relative to a control without HER2 inhibitor is indicative of the variant being sensitive to the inhibitor.

14. The method of claim 1 wherein said HER2 variant is obtained from a patient's biological sample consisting of blood, serum, and tumor tissue.

15. The method of claim 1, wherein said HER2 variant is transiently transfected.

16. A method of determining whether an HER2 variant is sensitive to treatment with an HER2 inhibitor in a cell, comprising the steps of:

a) preparing a cDNA encoding said HER2 variant;

b) preparing an expression cassette containing the HER2 variant cDNA;

c) transfecting said prepared expression cassette containing said HER2 variant cDNA in an assay cell having a stably integrated JNK reporter construct having SEQ ID NO: 31 comprising a reporter gene cDNA linked to 6 AP-1 binding sites, said assay cell having a stably integrated HER3 expression construct; and said assay cell having a HER1 and HER2 double knockout, wherein the HER2 variant and HER3 are expressed;

d) exposing said transfected cell to a HER activator, wherein HER3 complexes with said HER2 variant to form a dimer which thereby activates the JNK reporter construct and generates a signal;

e) exposing said transfected cell with an HER2 inhibitor; and f) determining whether said HER2 variant is sensitive to treatment with said HER2 inhibitor by measuring a change in signal.

* * * * *